(12) United States Patent
Schuster et al.

(10) Patent No.: US 11,623,193 B2
(45) Date of Patent: Apr. 11, 2023

(54) SYSTEM AND METHOD OF METASTABLE STATE MIXING

(71) Applicant: NCH Life Sciences LLC, Irving, TX (US)

(72) Inventors: Michael J. Schuster, Shorewood, IL (US); Dwayne A. Porter, Lockport, IL (US); Douglas C. Saunders, Plainfield, IL (US); Jeffrey W. Siegrist, West Chicago, IL (US); Thomas R. Bajek, Naperville, IL (US)

(73) Assignee: NCH Life Sciences LLC, Irving, TX (US)

( * ) Notice: Subject to any disclaimer, the term of this patent is extended or adjusted under 35 U.S.C. 154(b) by 524 days.

(21) Appl. No.: 16/552,142

(22) Filed: Aug. 27, 2019

(65) Prior Publication Data

US 2020/0078751 A1 Mar. 12, 2020

Related U.S. Application Data

(60) Provisional application No. 62/723,339, filed on Aug. 27, 2018.

(51) Int. Cl.
*C12M 1/36* (2006.01)
*B01F 35/22* (2022.01)
(Continued)

(52) U.S. Cl.
CPC .......... *B01F 35/2209* (2022.01); *A01G 31/02* (2013.01); *A01K 7/025* (2013.01);
(Continued)

(58) Field of Classification Search
CPC ..................................................... C12M 21/00
(Continued)

(56) References Cited

U.S. PATENT DOCUMENTS 4,989,641 A 2/1991 Jones et al.
2001/0016631 A1 8/2001 Freitag et al.
(Continued)

FOREIGN PATENT DOCUMENTS

WO 2017037072 A1 3/2017

OTHER PUBLICATIONS

International Search Report and Written Opinion dated Dec. 27, 2019 for PCT Patent Applicatoin No. PCT/ US19/48263.
(Continued)

*Primary Examiner* — David L Sorkin
(74) *Attorney, Agent, or Firm* — Thomas | Horstemeyer, LLP

(57) ABSTRACT

Metastable state spore incubation mixing systems are described. An example system includes a spores container to store spores, a nutrient container to store nutrients, a water supply line, a syringe tank, a syringe pump, an adjustable valve, a heater, and a controller. In a drawing phase of the system, a controller can cause the syringe pump and the adjustable valve to draw into the syringe tank a volume of spores, nutrients, and water to form a mixture. The controller causes the heater to heat the mixture for a period of time. In a dispensing phase of the system, the controller can cause the syringe pump to expel the mixture through the adjustable valve and into a water distribution system. The controller can direct the system through a number of other phases of operation.

20 Claims, 34 Drawing Sheets

(51) Int. Cl.
  *B65D 33/01* (2006.01)
  *A01G 31/02* (2006.01)
  *A01K 7/02* (2006.01)
  *C12N 1/00* (2006.01)
  *B01F 35/93* (2022.01)
  *B01F 35/21* (2022.01)
  *B01F 35/75* (2022.01)
  *B01F 35/71* (2022.01)
  *B01F 35/90* (2022.01)
  *B01F 101/18* (2022.01)

(52) U.S. Cl.
  CPC .......... *A01K 7/027* (2013.01); *B01F 35/2115* (2022.01); *B01F 35/21112* (2022.01); *B01F 35/717613* (2022.01); *B01F 35/718051* (2022.01); *B01F 35/75471* (2022.01); *B01F 35/93* (2022.01); *B65D 33/01* (2013.01); *C12N 1/00* (2013.01); *B01F 2035/99* (2022.01); *B01F 2101/18* (2022.01)

(58) Field of Classification Search
  USPC ....................................................... 435/243
  See application file for complete search history.

(56) References Cited

U.S. PATENT DOCUMENTS

| | | |
|---|---|---|
| 2002/0059945 A1 | 5/2002 | Maiefski et al. |
| 2003/0095897 A1 | 5/2003 | Grate et al. |
| 2004/0232069 A1* | 11/2004 | Shaffer ............ C12M 41/36 210/610 |
| 2005/0032032 A1* | 2/2005 | Pearce, III ......... C12M 41/12 435/286.5 |
| 2005/0244299 A1 | 11/2005 | Dasgupta et al. |
| 2010/0009871 A1 | 1/2010 | Reed et al. |
| 2010/0255569 A1 | 10/2010 | Maranhao |
| 2017/0144155 A1 | 5/2017 | Bohm et al. |
| 2017/0175070 A1 | 6/2017 | Boyette et al. |
| 2019/0100723 A1 | 4/2019 | Church et al. |

OTHER PUBLICATIONS

Office Action from Vietnamese Patent Application No. 1-2021-01516 dated Apr. 27, 2021.
Supplementary European Search Report dated Apr. 7, 2022 for European Patent Application No. 19855927.
Indonesian Office Action dated Oct. 11, 2022 for Indonesian Application No. P00202101966 filed on Mar. 17, 2021.

* cited by examiner

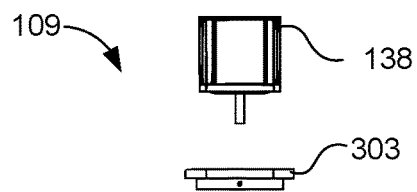
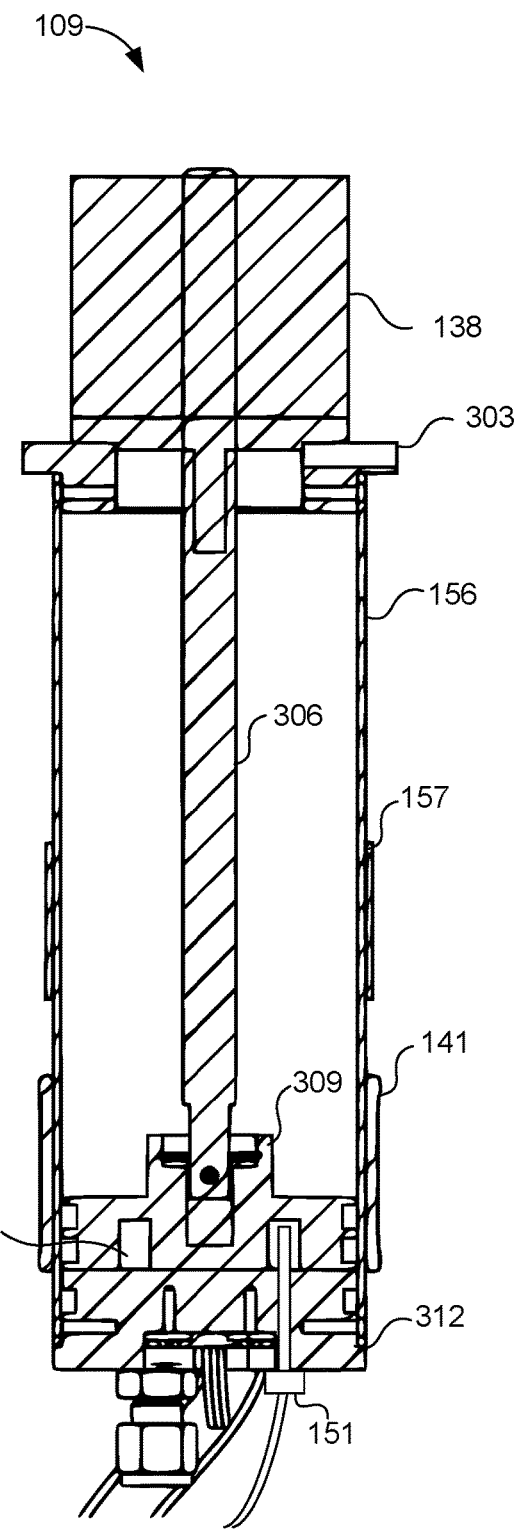
FIG. 3A  FIG. 3B

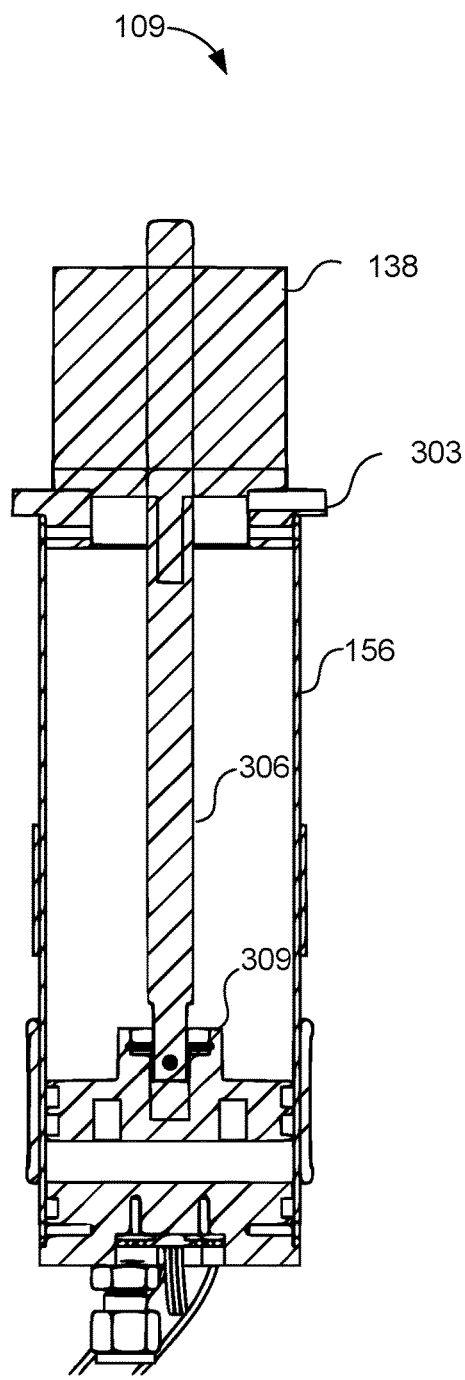
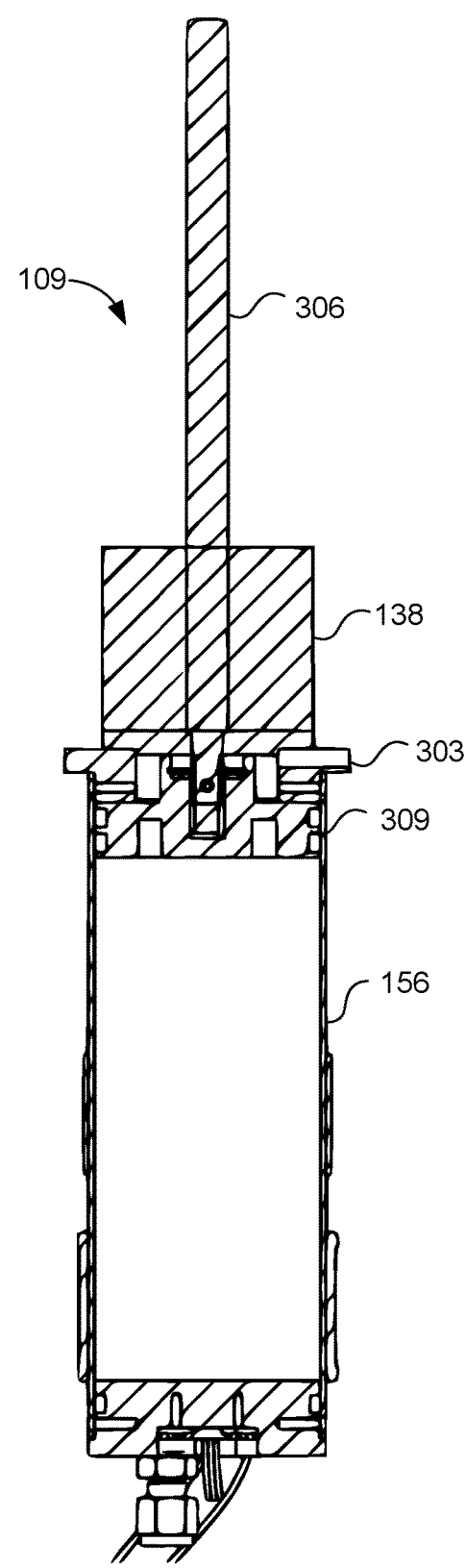
FIG. 3C  FIG. 3D

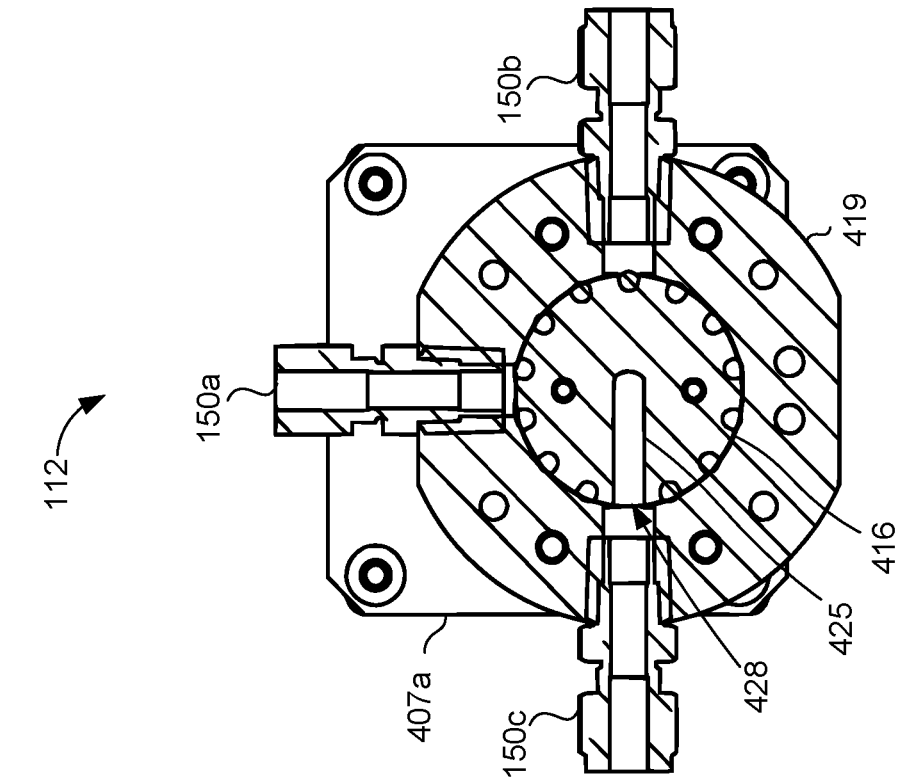
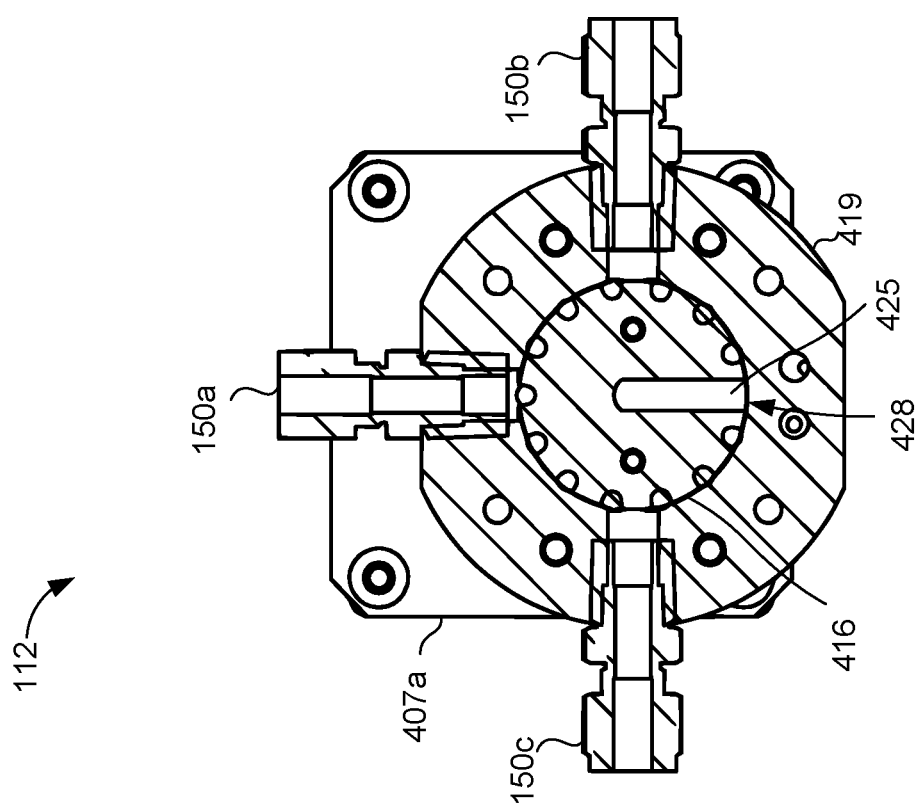

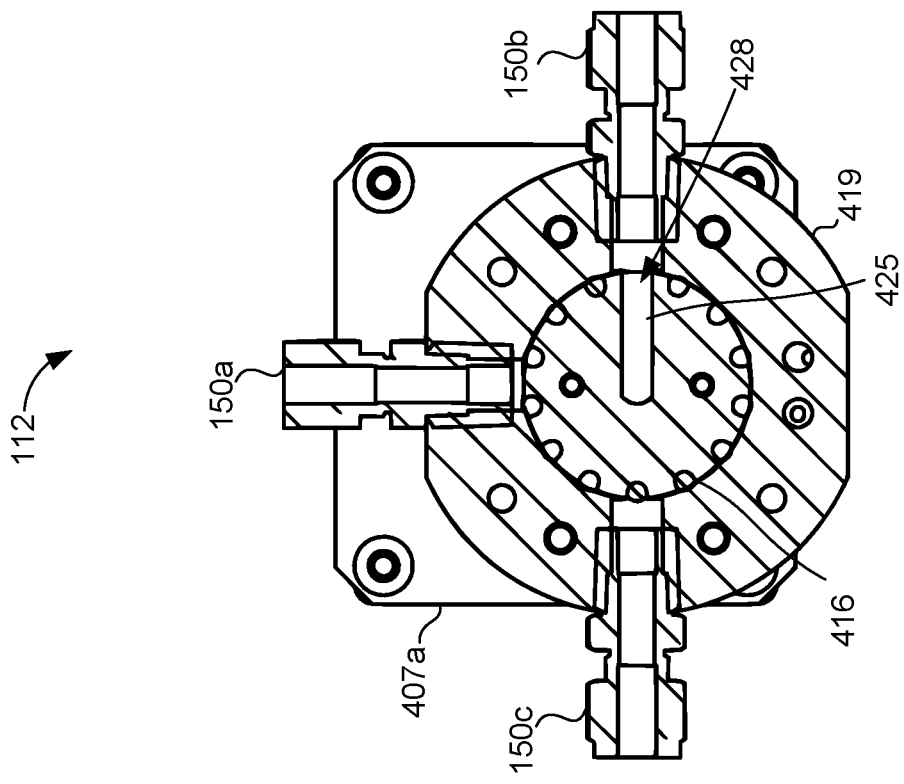
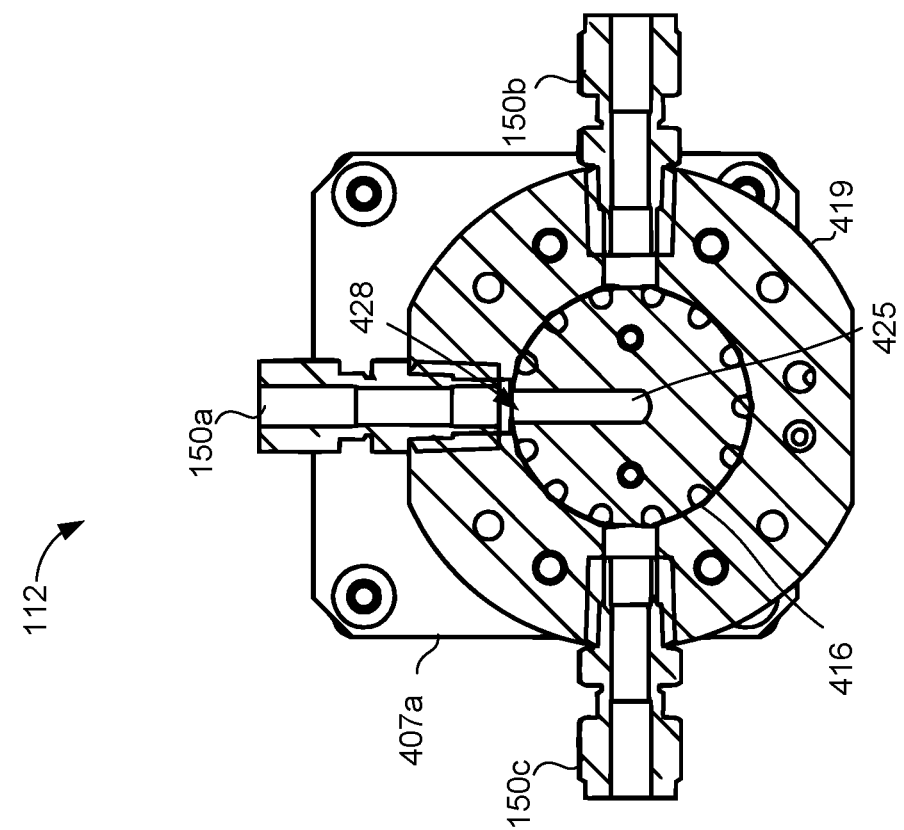

```
                    118
                      ↘         ┌─────────┐
                                │  START  │
                                └────┬────┘
                                     ▼
          ┌────────────────────────────────────────────────────────┐
          │       Detect trigger condition to execute system       │
          │                          503                           │
          └────────────────────────┬───────────────────────────────┘
                                   ▼
          ┌────────────────────────────────────────────────────────┐
          │   Detect that the adjustable valve is at the neutral position   │
          │                          506                           │
          └────────────────────────┬───────────────────────────────┘
                                   ▼
          ┌────────────────────────────────────────────────────────┐
          │  Draw spores into the tank using the syringe pump and the adjustable valve  │
          │                          509                           │
          └────────────────────────┬───────────────────────────────┘
                                   ▼
          ┌────────────────────────────────────────────────────────┐
          │ Draw nutrients into the tank using the syringe pump and the adjustable valve │
          │                          512                           │
          └────────────────────────┬───────────────────────────────┘
                                   ▼
          ┌────────────────────────────────────────────────────────┐
          │  Draw water into the tank using the syringe pump and the adjustable valve   │
          │                          515                           │
          └────────────────────────┬───────────────────────────────┘
                                   ▼
          ┌────────────────────────────────────────────────────────┐
          │     Heat the mixture in the tank to a temperature using a heater    │
          │                          518                           │
          └────────────────────────┬───────────────────────────────┘
                                   ▼
          ┌────────────────────────────────────────────────────────┐
          │          Draw water into the tank to cool down mixture           │
          │                          521                           │
          └────────────────────────┬───────────────────────────────┘
                                   ▼
          ┌────────────────────────────────────────────────────────┐
          │      Expel mixture into water supply line using the syringe pump      │
          │                          524                           │
          └────────────────────────┬───────────────────────────────┘
                                   ▼
          ┌────────────────────────────────────────────────────────┐
          │           Draw water from water source to rinse tank            │
          │                          527                           │
          └────────────────────────┬───────────────────────────────┘
                                   ▼
          ┌────────────────────────────────────────────────────────┐
          │       Expel water into water supply line to purge the tank       │
          │                          530                           │
          └────────────────────────┬───────────────────────────────┘
                                   ▼
                                ┌─────┐
                                │ END │
                                └─────┘
```

FIG. 5

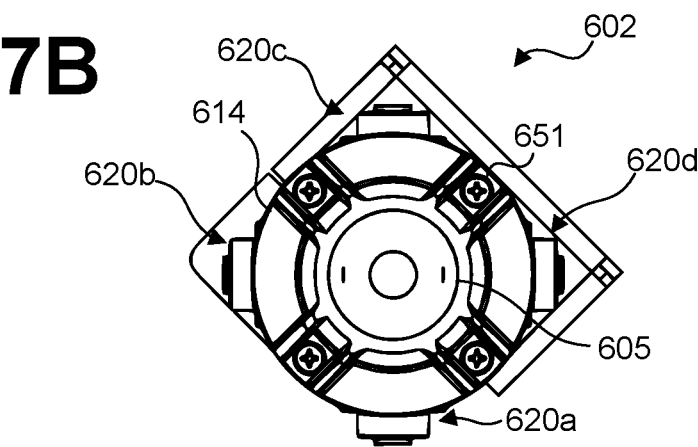
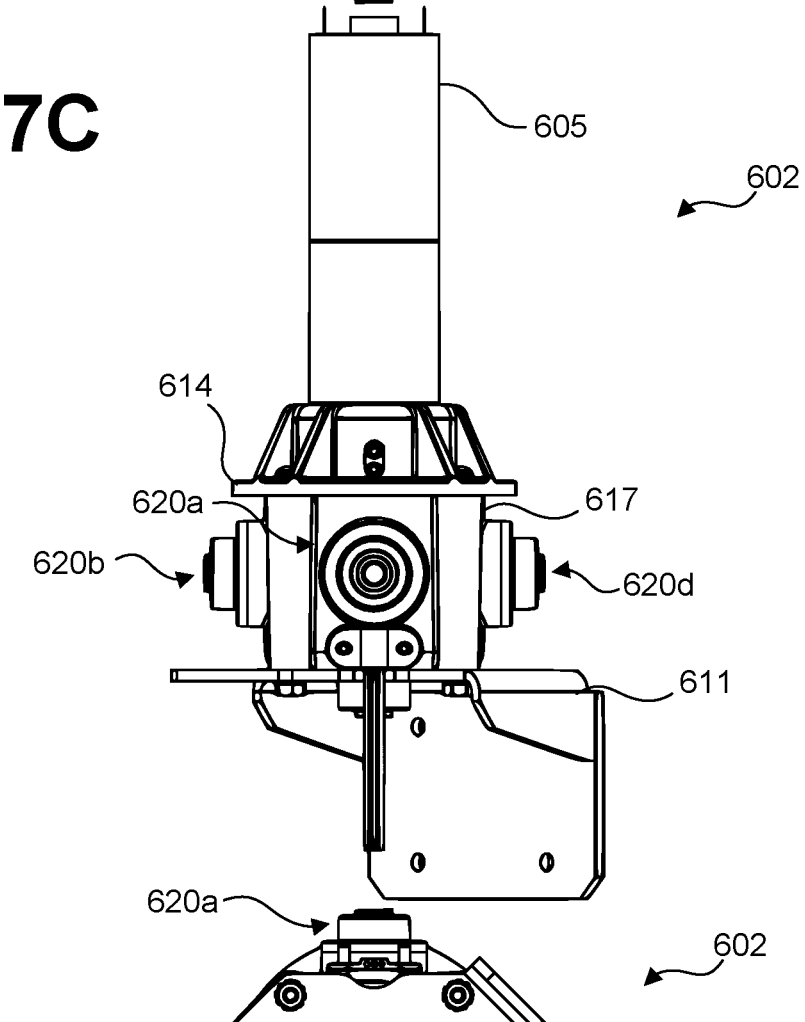
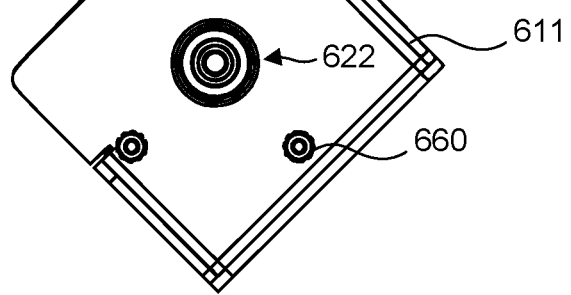

FIG. 9A
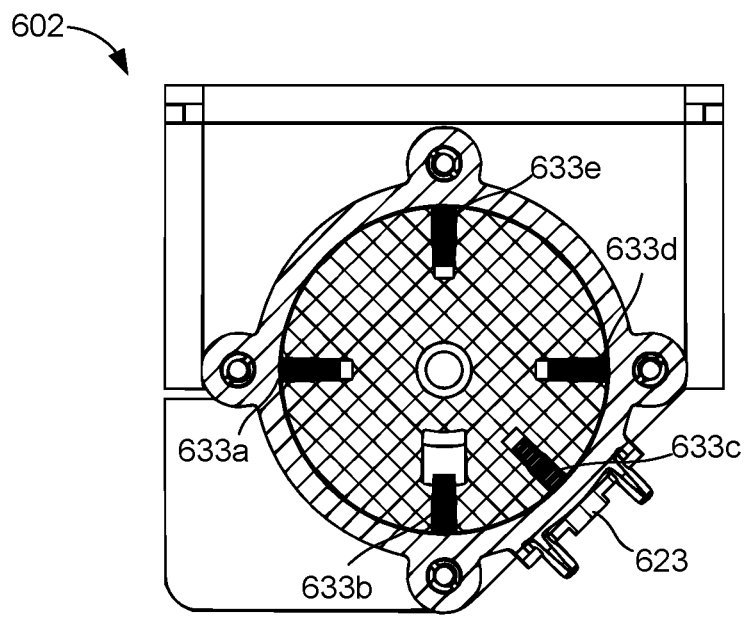
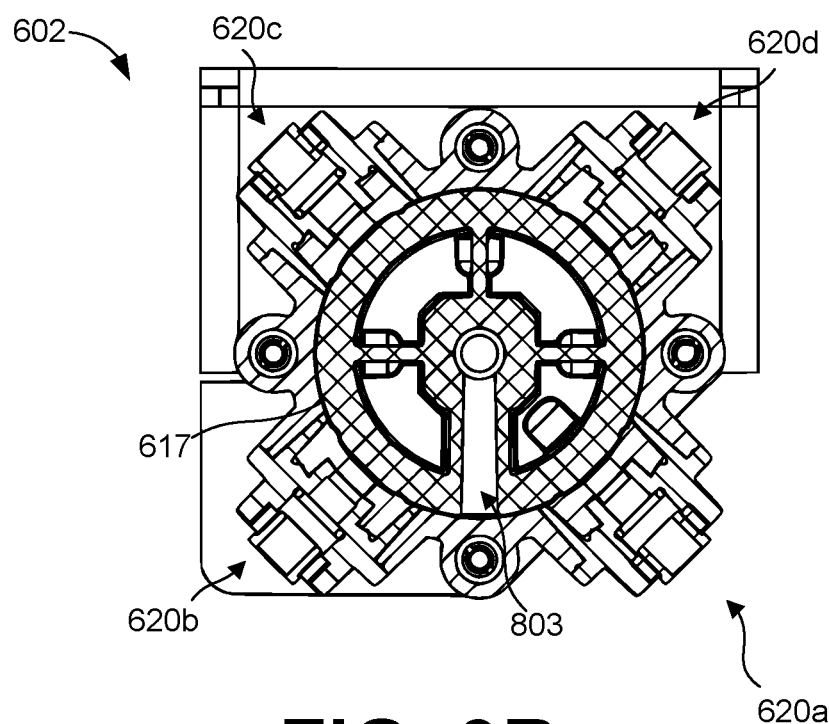
FIG. 9B

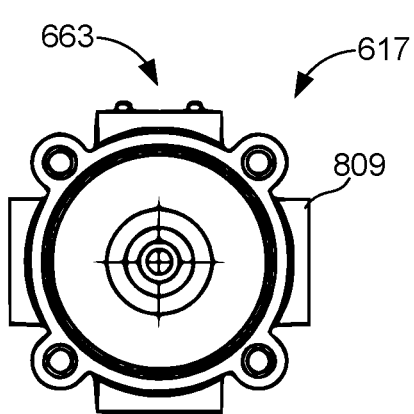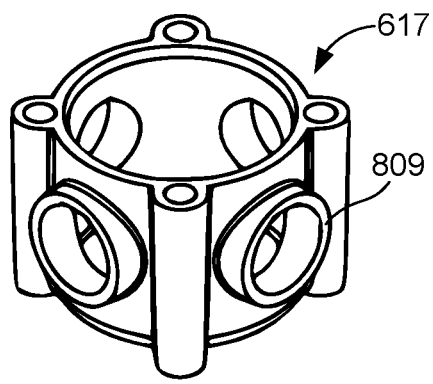
FIG. 10A  FIG. 10B
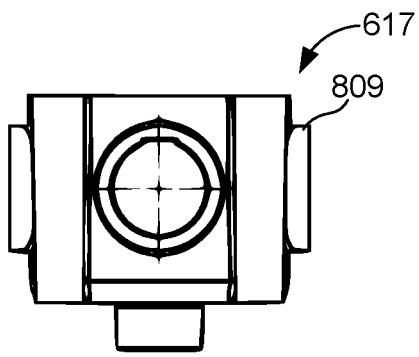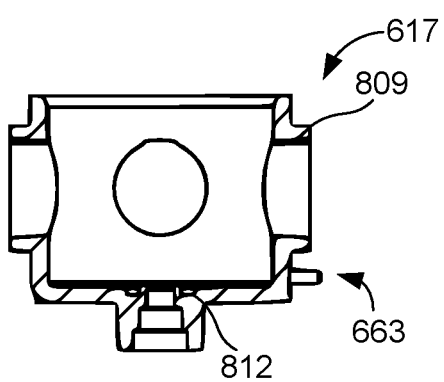
FIG. 10C  FIG. 10D
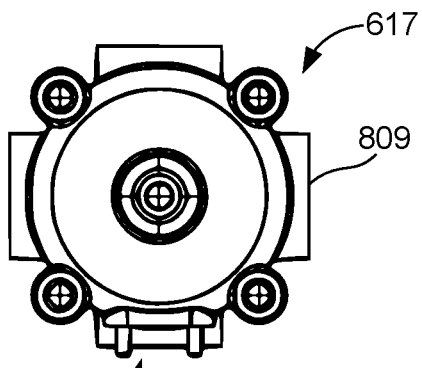
FIG. 10E
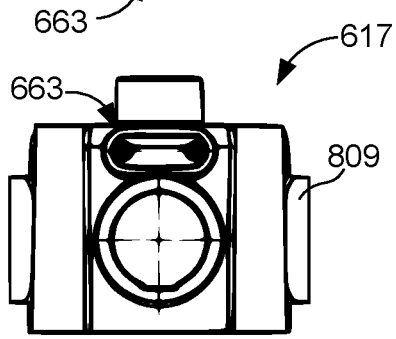
FIG. 10F

FIG. 11A
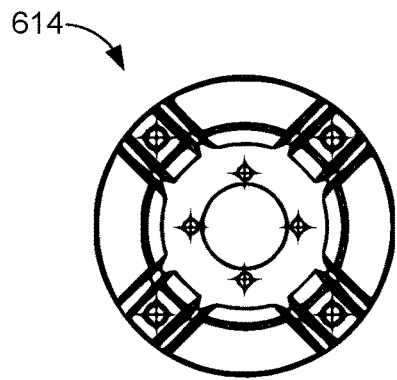
FIG. 11B
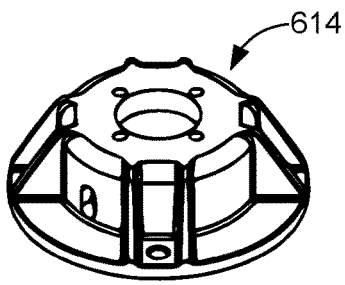
FIG. 11C
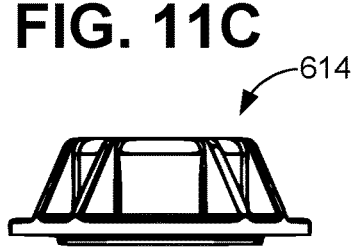
FIG. 11D
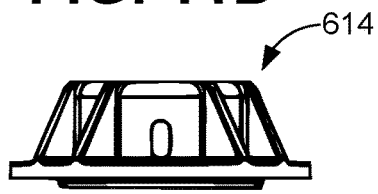
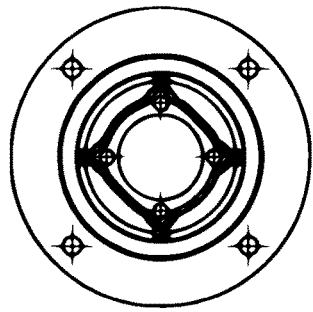
FIG. 11E
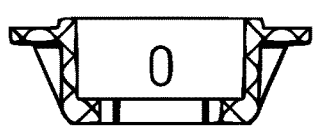
FIG. 11F

FIG. 12C
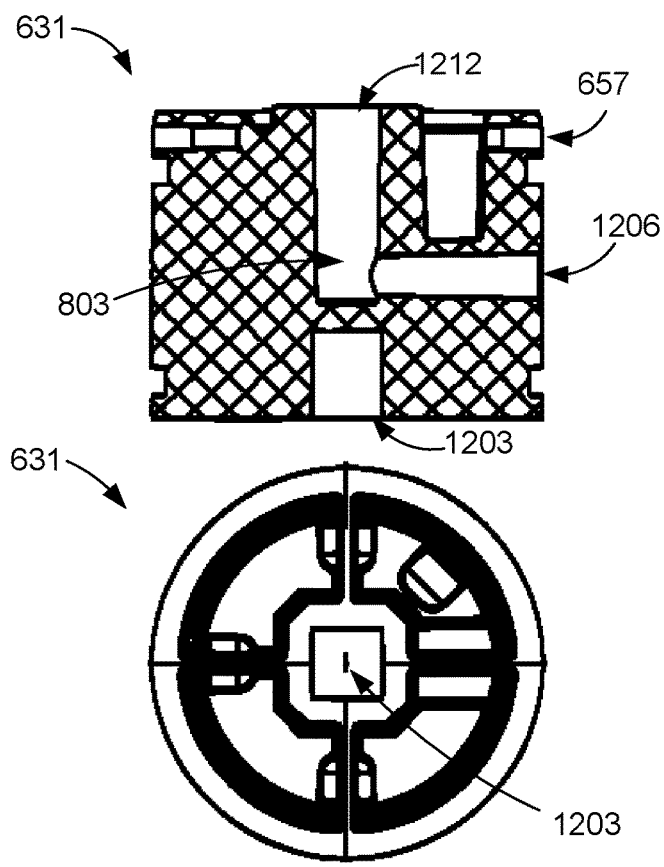
FIG. 12B
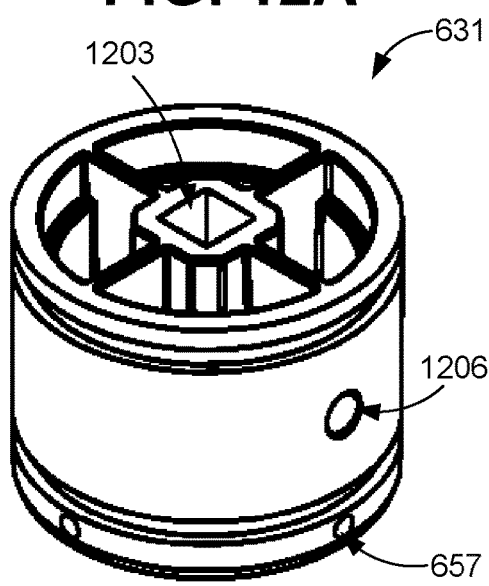
FIG. 12A

FIG. 12D
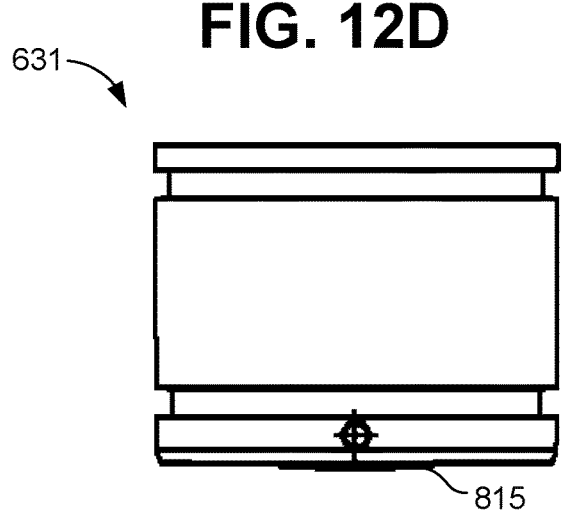
FIG. 12E
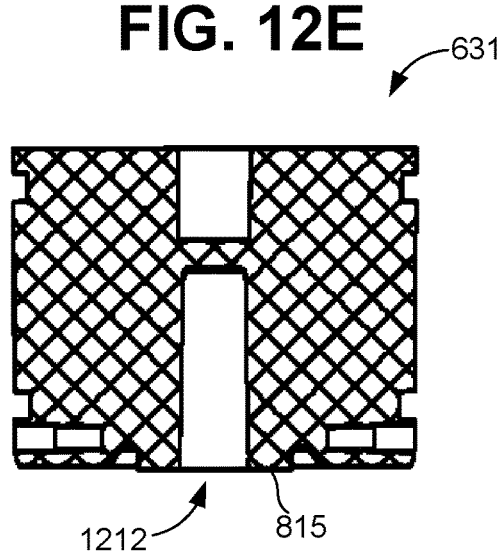
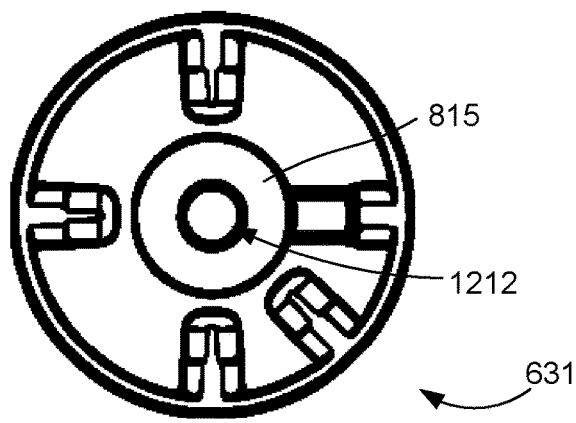
FIG. 12F

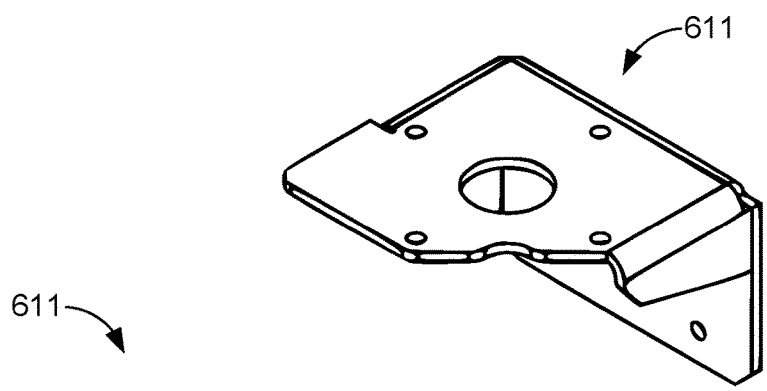
FIG. 15A
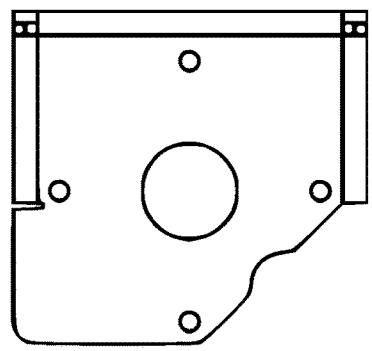
FIG. 15B
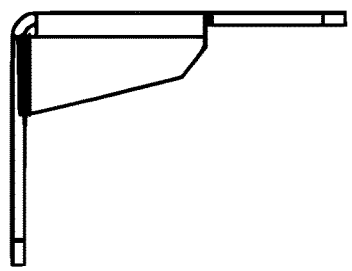
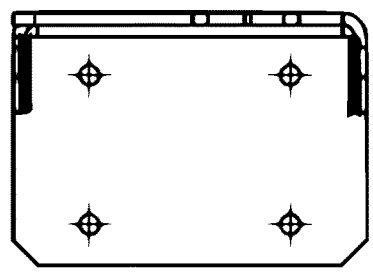
FIG. 15C    FIG. 15D

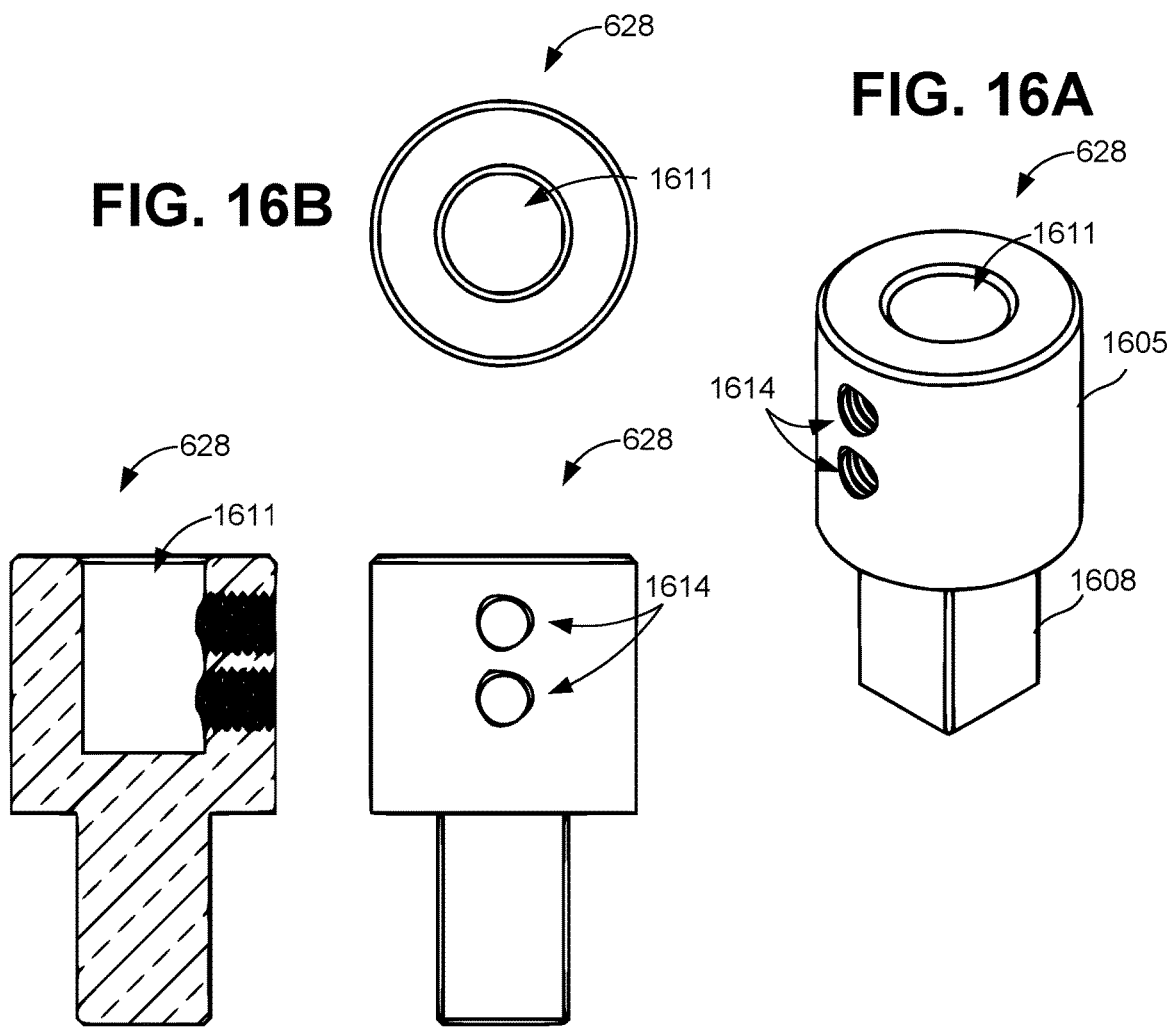
FIG. 16B　　FIG. 16A
FIG. 16C　　FIG. 16D
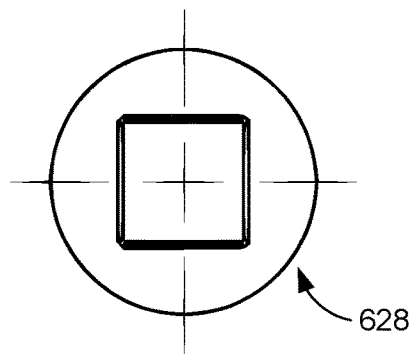
FIG. 16E

```
                    118
                      ↘         ( START )
                                    ↓
                    ┌─────────────────────────────────────────────────┐
                    │ Detect trigger condition to execute system      │
                    │ 1703                                            │
                    └─────────────────────────────────────────────────┘
                                    ↓
                    ┌─────────────────────────────────────────────────┐
                    │ Detect that the adjustable valve is at the neutral position │
                    │ 1706                                            │
                    └─────────────────────────────────────────────────┘
                                    ↓
                    ┌─────────────────────────────────────────────────┐
                    │ Move adjustable valve to water inlet and draw water into the tank │
                    │ 1709                                            │
                    └─────────────────────────────────────────────────┘
                                    ↓
                    ┌─────────────────────────────────────────────────┐
                    │ Move adjustable valve to spore port and draw nutrients into the tank │
                    │ 1712                                            │
                    └─────────────────────────────────────────────────┘
                                    ↓
                    ┌─────────────────────────────────────────────────┐
                    │ Move adjustable valve to nutrient port and draw spores into the tank │
                    │ 1715                                            │
                    └─────────────────────────────────────────────────┘
                                    ↓
                    ┌─────────────────────────────────────────────────┐
                    │ Move adjustable valve to water inlet and draw water into the tank │
                    │ 1718                                            │
                    └─────────────────────────────────────────────────┘
                                    ↓
                    ┌─────────────────────────────────────────────────┐
                    │ Move adjustable valve to water outlet and agitate mixture in tank │
                    │ 1721                                            │
                    └─────────────────────────────────────────────────┘
                                    ↓
                    ┌─────────────────────────────────────────────────┐
                    │ Heat the mixture in the tank to a temperature using a heater │
                    │ 1724                                            │
                    └─────────────────────────────────────────────────┘
                                    ↓
                    ┌─────────────────────────────────────────────────┐
                    │ Move adjustable valve to water inlet and draw water into the tank │
                    │ 1727                                            │
                    └─────────────────────────────────────────────────┘
                                    ↓
                    ┌─────────────────────────────────────────────────┐
                    │ Move adjustable valve to water outlet and expel mixture to distribution system │
                    │ 1730                                            │
                    └─────────────────────────────────────────────────┘
                                    ↓
                    ┌─────────────────────────────────────────────────┐
                    │ Move adjustable valve to water inlet and draw water into the tank for rinsing │
                    │ 1733                                            │
                    └─────────────────────────────────────────────────┘
                                    ↓
                    ┌─────────────────────────────────────────────────┐
                    │ Move adjustable valve to water outlet and expel water for purging │
                    │ 1736                                            │
                    └─────────────────────────────────────────────────┘
                                    ↓
                                 ( END )                     FIG. 17
```

SYSTEM AND METHOD OF METASTABLE STATE MIXING

CROSS REFERENCE TO RELATED APPLICATIONS

This application claims the benefit of, and priority to, U.S. Provisional Patent Application No. 62/723,339, entitled "SYSTEMS AND METHOD OF METASTABLE STATE MIXING," filed on Aug. 27, 2018, which is hereby incorporated herein by reference in its entirety.

BACKGROUND

Germination is a process in which an organism grows, often out from a structure similar to a seed. A seedling sprouting from a seed of an angiosperm or gymnosperm is one example of germination. Similarly, the growth of a sporeling, which is a young plant or fungus produced by a germinated spore, is also an example of germination. Thus, germination can refer to the emergence of cells from resting spores and the growth of sporeling hyphae or thalli, for example, from spores in fungi, algae, and some plants. For some spores, germination can involve cracking or opening the relatively thick cell wall of a dormant spore. For example, in zygomycetes, the thick-walled zygosporangium cracks open and the zygospore inside gives rise to the emerging sporangiophore. Generally, germination can be thought to encompass the growth of any organization from a small existence or germ into a greater being.

SUMMARY

Embodiments of the present disclosure are related to systems and methods for metastable state spore incubation mixing. Additionally, the embodiments described herein can also be used for water treatment, drain treatment, and dispensing biologicals or chemicals.

According to one embodiment, among others, a system is provided comprising a spores container to store a solution of spores, a nutrient container to store a solution of nutrients, a water source, and a syringe pump comprising a tank. The tank is configured to receive a volume of the solution of spores, a volume of the solution of nutrients, and a volume of water. The system also comprises a heater, an adjustable valve, and a controller.

The heater heats a mixture of the solution of spores, the volume of the solution of nutrients, and the volume of water in the tank. The adjustable valve is configured to controllably open and close a first channel from the tank to the spores container, a second channel from the tank to the nutrient container, and a third channel from the tank to the water source. The controller is configured to control a sequence of operations among the adjustable valve and the syringe pump to form and activate a dosage of the mixture. The syringe pump is configured to draw the volume of the solution of spores, the volume of the solution of nutrients, and the volume of water from the adjustable valve and into the tank. The syringe pump is configured to expel the mixture from the tank to the adjustable valve.

According to one embodiment, among others, a method is provided comprising the step of opening, via a controller, a first channel of an adjustable valve from a tank of a syringe pump to a spores container and drawing, via the controller, a volume of spores into the tank from the spores container using the syringe pump. The method also comprises the steps of opening, via a controller, a second channel of the adjustable valve from the tank of the syringe pump to a nutrient container and drawing, via the controller, a volume of nutrients into the tank from the nutrient container using the syringe pump. The method also comprises the steps of opening, via a controller, a third channel of the adjustable valve from the tank of the syringe pump to a water supply line and drawing, via the controller, a volume of water into the tank from the water supply line using the syringe pump. The method also comprises the steps of heating, via the controller, a mixture of the volume of spores, the volume of nutrients, and the volume of water in the tank. The mixture is heated with a heater controlled by the controller. The method also comprises the step of expelling, via the controller, the mixture from the tank to the adjustable valve using the syringe pump.

According to one embodiment, among others, an adjustable valve is provided comprising a valve cover that comprises a first cover aperture that connects to a first port, a second cover aperture that connects to a second port, and a third cover aperture that connects to a third port. The adjustable valve also includes a valve base that attaches to the valve cover. The valve base comprises a forth aperture that connects to a fourth port. The adjustable valve also comprises a valve core that is positioned inside of the valve base. The valve core comprises a channel aperture along a perimeter of the valve core. The adjustable valve comprises a motor that attaches to the valve cover and attaches to the valve core. The motor rotates the channel aperture to open and close a first channel from the first port to the fourth port, a second channel from the second port to the forth port, and a third channel from the third port to the fourth port.

According to one embodiment, among others, an adjustable valve is provided comprising a motor, a valve base, and a valve core. The valve base comprises a container with an inner cavity, and the valve base also comprises a first side port, a second side port, a third side port and a tank port. The valve core is configured to rotate the valve core within the inner cavity of the valve base. The valve base comprises a core port opening and a tank opening that are connected to a fluid channel. The valve core is rotated to align the core port opening with at least one of the first port, the second port or the third port. The tank port of the valve base can be aligned with the tank opening of the valve core.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

In addition, all optional and preferred features and modifications of the described embodiments are usable in all aspects of the entire disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

FIGS. 3A through 3D illustrate various views of a syringe pump according to one embodiment described herein.

FIG. 5 is a flowchart illustrating examples of functionality implemented as portions of a controller operating in metastable state spore incubation mixing system of FIG. 1A according to various embodiments of the present disclosure.

FIGS. 7A through 7D illustrate various views of the adjustable valve assembly from FIG. 6 according to various embodiments of the present disclosure.

FIGS. 9A through 9J illustrate various cross-sectional views of the adjustable valve from FIG. 8 according to various embodiments of the present disclosure.

FIGS. 10A through 10F illustrate various views of the valve base from FIG. 7A according to various embodiments of the present disclosure.

FIGS. 11A through 11F illustrate various views of the motor mount from FIG. 7A according to various embodiments of the present disclosure.

FIGS. 12A through 12F illustrate various views of the valve base from FIG. 7A according to various embodiments of the present disclosure.

FIGS. 13A through 13F illustrate various views of the port from FIG. 7A according to various embodiments of the present disclosure.

FIGS. 14A through 14F illustrate various views of the gasket from FIG. 7A according to various embodiments of the present disclosure.

FIGS. 15A through 15D illustrate various views of the mounting bracket from FIG. 7A according to various embodiments of the present disclosure.

FIGS. 16A through 16E illustrate various views of the motor coupler from FIG. 7A according to various embodiments of the present disclosure.

FIG. 17 is a flowchart illustrating examples of functionality implemented as portions of a controller operating in metastable state spore incubation mixing system of FIG. 1A according to various embodiments of the present disclosure.

DETAILED DESCRIPTION

As noted above, germination is a process in which an organism grows, often out from a structure similar to a seed. In that context, spore germination is a process where spores effectively wake-up or are revived from a dormant state to a vegetative growth state. The first step in this process is one by which spores are activated and are induced to germinate, typically by an environmental signal called a germinant. This signal can be a nutrient such as an L-amino acid, among other types of nutrients. Nutrient germinants bind to receptors in the inner-membrane of the spore to initiate germination. Additionally, sugars have been shown to increase the binding affinity of L-amino acids for their cognate receptors.

The germinant signal initiates a cascade of events for the spore, such as the release of certain acids, the absorption of water, and an outgrowth stage including the initiation of the metabolic, biosynthetic, and deoxyribonucleic acid (DNA) replication and repair pathways. A ripening period occurs during the outgrowth stage in which molecular machinery (e.g., transcription factors, translation machinery, biosynthesis machinery, etc.) is activated but no morphological changes (e.g., such as cell growth) occur. The ripening period can vary in length based on the resources packaged with the spore during the process of sporulation. For example, the preferred carbon source of several *Bacillus* species typically contain a pool of malate that is used during the revival process. After the outgrowth step, spore revival is complete and cells are considered to be vegetatively growing. Between the dormant and vegetative growth states in the germination process, spores progress through a type of metastable state in which the spores are no longer dormant but also not yet in the vegetative growth phase.

The embodiments described herein are directed to various aspects of metastable state spore incubation mixing systems. An example system includes a spores container to store spores, a nutrient container to store nutrients, a water supply line, a syringe pump, an adjustable valve, heating elements, and a controller. The controller can control the various components of the system. Initially, the controller can determine from sensor readings that a plunger for the syringe pump and the adjustable valve are in a neutral state. The controller may cause the plunger to create a vacuum in the syringe pump to relieve water pressure in the syringe pump, the adjustable valve, and/or other components of the system. In a dosage phase of the system, the controller can actuate the adjustable valve to open and close a first channel from the syringe pump to the spores container, a second channel from the syringe pump to the nutrient container, and a third channel from the syringe pump to the water supply line in a sequence. When a channel is open, the controller can cause the syringe pump and the adjustable valve to draw a volume of spores, nutrients, and water into the syringe pump to form a mixture. Then, the controller can cause a heater to heat the mixture for a period of time to activate spores in the mixture. If a cooling phase is required, the syringe pump and the adjustable valve can draw water into the syringe pump from the water supply line. The mixture can then be allowed to cool for a period of time. In a dispensing phase of the system, the controller can cause the syringe pump to expel the mixture through the adjustable valve and into a water distribution system as drinking water for animals. In that context, the controller can control the rate and amount of the mixture provided to a water distribution system for animals, in which the rate and amount can depend upon an animal size, a development stage of an animal (e.g. baby, full size, etc.), the number of animals, the type of animal, a time of day, an ambient temperature for an area for an animal, a sunrise time, animal activity, and other factors. In some example implementations, the system may be designed for mixing a dosage for plant consumption and/or human consumption. The rate and amount of the mixture provided to the water distribution system may also depend on plant consumption factors, such as a type of plant, number of plants, a size of a plant, an ambient plant temperature, soil conditions, and other suitable plant factors. Likewise, the rate and amount of the mixture provided to the water distribution system may also depend on human consumption factors, such as a height and weight of a person, gender, a number of people, and other suitable human factors. The controller can direct the system through a number of other phases of operation. Additionally, the embodiments described herein can also be used for water treatment, drain treatment, and dispensing biologicals or chemicals.

Figure 1A:
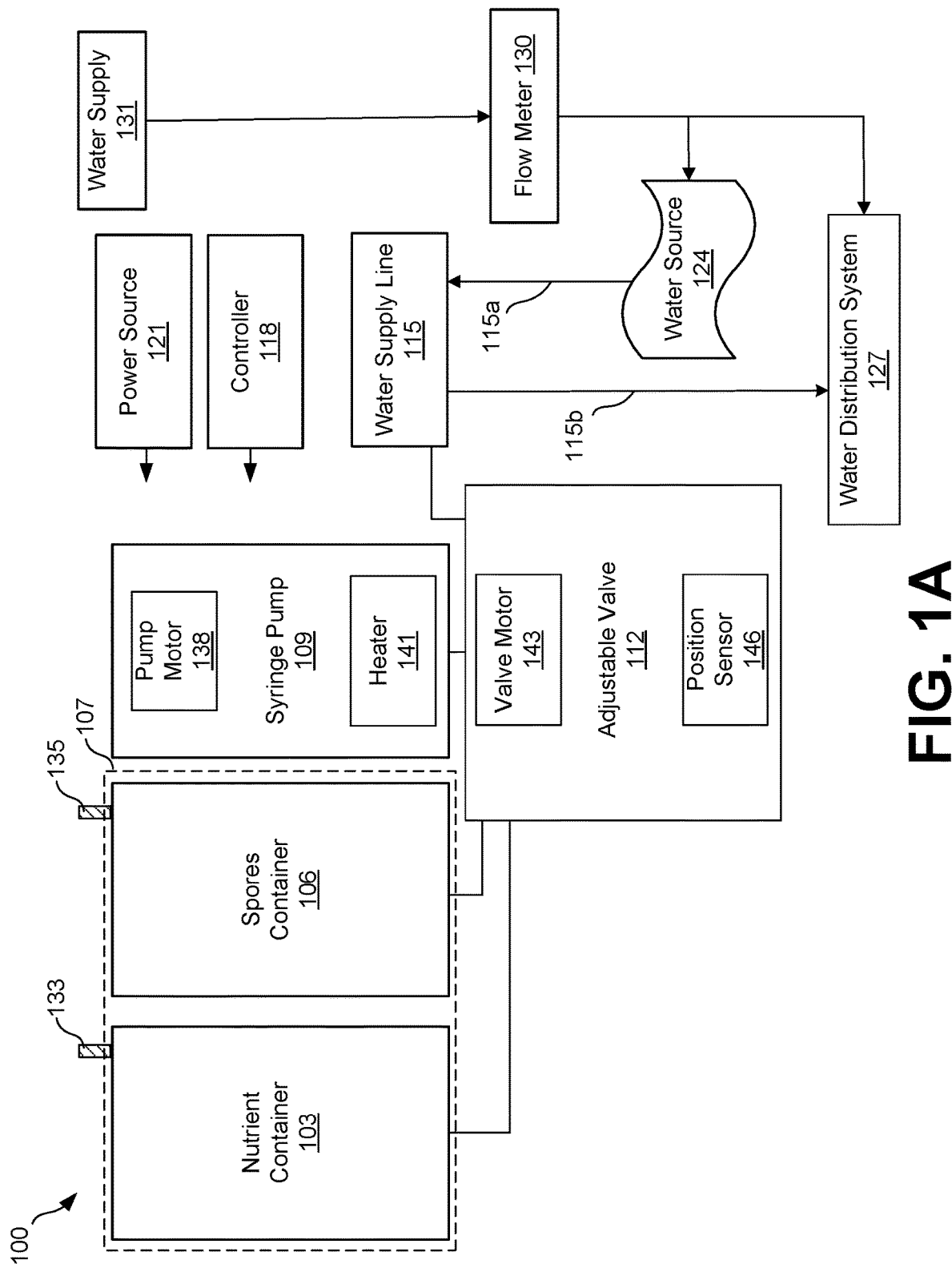
FIGS. 1A and 1B illustrate an example metastable state spore incubation mixing system according to one embodiment described herein.

Turning to the drawings, FIG. 1A illustrates a block diagram of an example metastable state spore incubation mixing system 100 ("system 100") according to various embodiments described herein. In FIG. 1A, the system 100 is representative of the types of components that can be used for metastable state spore incubation mixing. The parts or components are not drawn to scale in FIG. 1A. The arrangement of the parts or components is not intended to be limiting, as other arrangements consistent with the concepts described herein are within the scope of the embodiments. Further, the parts or components shown in FIG. 1A are not exhaustive. In other words, the system 100 can include other components. Similarly, certain components shown in FIG. 1A can be omitted in certain cases.

As shown in FIG. 1A, the system 100 includes a nutrient container 103, a spores container 106, a syringe pump 109, an adjustable valve 112, a water supply line 115, a controller 118, and a power source 121. Among other components, the system 100 also includes a water source 124, a water distribution system 127, and may or may not incorporate a flow meter 130. As one skilled in the art can appreciate, various tubes and valves can be used to connect the various components of the system 100.

The nutrient container 103 can be used to store a solution of nutrients, and the spore container 106 can be used to store a solution of spores. The solution of nutrients and the solution of spores can vary. The solutions discussed in the present disclosure are non-limiting examples that can be employed by the system 100.

The nutrient container 103 and the spore container 106 can be embodied as rigid, semi-rigid, or flexible containers formed from any suitable material or materials. If formed from a rigid or semi-rigid material, the nutrient container 103 and the spore container 106 can rely upon the vent caps 133 and 135 to pass air into the containers as the nutrients and the spores are drawn out of them by the syringe pump 109, thus relieving any positive or negative pressure in the containers. The vent caps 133 and 135 can thus include filters or membranes to remove particles from the air. In that way, the vent caps 133 and 135 can keep the contents of the nutrient container 103 and the spore container 106 from being contaminated with foreign particles and substances. A particular example of the nutrient container 103 and the spore container 106 is described below with reference to FIG. 1B. If the nutrient container 103 and the spore container 106 are formed from flexible materials, such as plastic bags, the vent caps 133 and 135 can be omitted, as the bags can collapse without any need to allow air to pass air into the containers. In some embodiments, the nutrient container 103 and the spores container 106 are a part of a dosage container 107. The dosage container 107 can be considered as a multi-chamber bottle. For example, a first chamber of the dosage container 107 can represent the nutrient container 103, and a second chamber can represent the spores container 106.

The syringe pump 109 can be used to expel and draw a volume of solution of spores, a volume of solution of nutrients, and a volume of water. The syringe pump 109 can include a pump motor 138 and a heater 141. The pump motor 138 can be controlled to operate a plunger within the syringe pump 109. The syringe pump 109 can also include a tank, a plunger, and other suitable pump components.

The heater 141 can be relied upon to heat a mixture of the solution of spores, the volume of the solution of nutrients, and the volume of water within the syringe pump 109. In a spore activation stage, the heater 141 can be configured to heat the mixture to a specified temperature range and hold the temperature within the specified temperature range for a period of time.

The adjustable valve 112 can be controlled to individually connect the syringe pump 109 with the spores container 106, the nutrient container 103, or the water supply line 115. The adjustable valve 112 may be comprised of materials such as stainless steel and other suitable metals. The adjustable valve 112 may also be comprised of material such as acrylonitrile butadiene styrene (ABS), polyvinyl chloride (PVC), polypropylene (PP), chlorinated polyvinyl chloride (CPVC), noryl polycarbonate, polyoxymethylene (POM), and other suitable plastic materials. The adjustable valve 112 may be constructed using an injection molded process, a machined process, and other suitable manufacturing processes. In some embodiments, the adjustable valve 112 can actuate the position of an interior elbow channel in order to open and close a fluid or gas channel between the syringe pump 109 and one of the nutrient container 103, the spores container 106, or the water supply line 115. The adjustable valve 112 can include a valve motor 143 and may include a position sensor 146. The valve motor 143 can be controlled to rotate or displace aspects of the adjustable valve 112 in order to open and close channels to the nutrient container 103, the spores container 106, and the water supply line 115. The position sensor 146 can be used to determine a position or orientation of the adjustable valve 112. As result, the position sensor 146 can serve as a feedback mechanism that verifies the present orientation of the adjustable valve 112, which can indicate whether a channel is opened or closed. For example, the adjustable valve 112 can be a rotatory valve. The position sensor 146 can determine that the rotatory valve has rotated 90 degrees from a neutral position. In some embodiments, the position sensor 146 may comprise a microswitch, a reed switch, a hall effect, a capacitive switch, a contact switch, and other suitable proximity switches. In some embodiments, the adjustable valve 112 may include a magnet, and the position sensor 146 can be used to detect a position or an orientation of the adjustable valve 112 based on the detection of the position or the orientation of the magnet. As one skilled in the art appreciates, other position sensors 146 can be used to detect the orientation or position of the adjustable valve 112.

The pump motor 138 and/or the valve motor 143 may be a stepper motor, a non-captive motor, a captive motor, a brushed motor, a brushless motor, a geared motor, a linear actuated motor, and other suitable motors as can be appreciated by one skilled in the arts. In some embodiments, the pump motor 138 and/or the valve motor 143 may have an encoder that monitors a position of the shaft 306 and/or monitors its position within a rotation cycle. The encoder may instruct the pump motor 138 to turn a particular number of degrees (e.g. 45 degrees, 60 degrees) in order to manipulate the plunger 309. The encoder may be a conductive encoder, an optical encoder, an on-axis magnetic encoder, an off-axis magnetic encoder, an absolute encoder, an incremental encoder, and other suitable encoders as can be appreciated by one skilled in the arts.

In one aspect, among others, the water supply line 115 can refer to an arrangement of tubes and valves for drawing in water from a water source 124 and into the syringe pump 109. The water source 124 can be a water tank or some other suitable water source 124. In another aspect, the water supply line 115 can refer to a conduit through which a mixture is expelled from the adjustable valve 112 to the water distribution system 127. The water distribution system 127 can refer to a water drinking apparatus for animals. For example, the water distribution system 127 may comprise a water line that leads to a water trough for animals. In some examples, a first water line can be used to dispense water into the water trough, and a second water line can be used to pull water from the water trough back to the adjustable valve 112. In another example, a single water supply line 115 may be used for pulling and dosing water into a water source 124 or a water distribution system 127. For example, a single water supply line 115 may be used to both pull water from a pond or a water trough and then supply a dosage mixture back into the pond or water trough. Other examples of water distribution systems 127 can include watering nipples, chicken waterers, livestock water tanks, water tubs, and other suitable means for providing water to animals. In some instances, the water source 124 can be a pressurized water supply, and in other cases, the water source 124 can be non-pressurized. In some embodiments, the system 100 may include a water supply 131 that supplies a flow of water to the water source 124 and/or the water distribution system 127. In some scenarios, when water is drawn by the system 100, the water may be drawn from the water source 124, which in turn is supplied water from the water supply 131. In other scenarios, when water is or is not being drawn by the system 100, the water supply 131 provides water to the water distribution system 127.

The controller 118 can be relied upon to control a sequence of operations among the adjustable valve 112 and the syringe pump 109 to form and activate a dosage of a mixture of the nutrients, the spores, and water. The controller 118 can provide control signals to individual components in the system 100 to direct the operation of each component. For example, the controller 118 can initiate a dosage cycle for the system 100 based on various triggering factors. In one instance, the controller 118 can configure a timer to trigger a dosage cycle based on a day and/or a time of day. In another example, the controller 118 may initiate a dosage cycle based on a motion sensor that detects an animal near the water distribution system 127. The controller 118 can include a processor, sensors, and various electronic components.

The power source 121 can include electronic components for supplying power to the components of the system 100. In some scenarios, the power source 121 may be a battery. In other scenarios, the power source 121 can represent an alternative current (AC) power source that is regulated to provide direct current (DC) voltages suitable for each of the components of the system 100.

The flow meter 130 can operate to measure water consumption for the water distribution system 127. In one example scenario, the flow meter 130 can provide water consumption data to the controller 118, which can be used by the controller 118 to initiate a dosage cycle, determine a frequency for initiating multiple dosage cycles over a time period, determine a dosage amount, and other suitable dosage conditions. In other scenarios, the water consumption data can be used to generate a water consumption profile for particular animals, farm locations, and other water conditions. Thus, the flow meter 130 can operate as a feedback mechanism for the controller 118 with respect to when to initiate a dosage cycle and with respect to the dosage rate. Other non-limiting examples of feedback components include a light sensor, an acoustic sensor, a motion sensor, a proximity sensor, and other suitable sensing devices that can be used to detect the presence or activity of one or more animals.

Figure 1B:
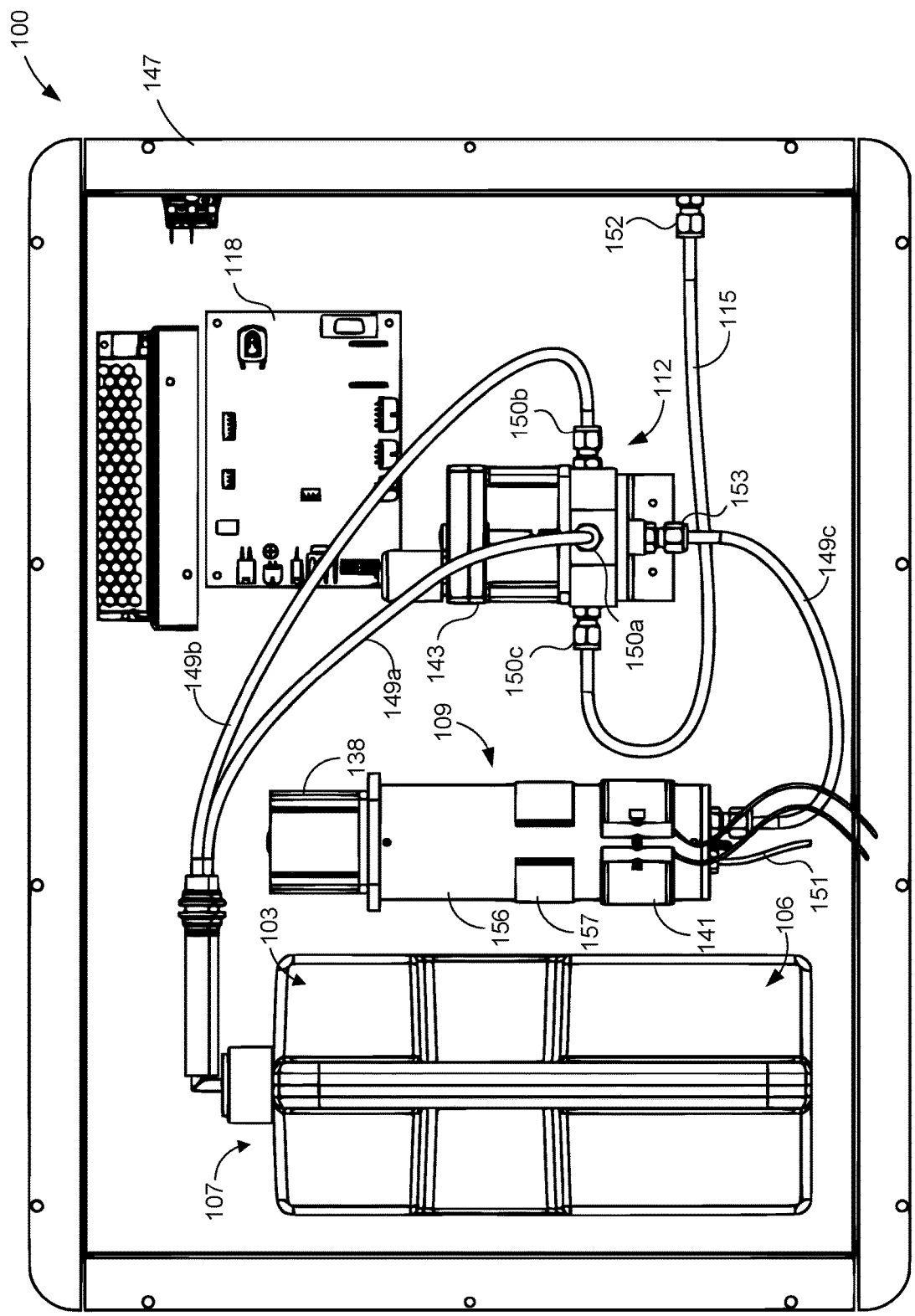
Figure 1C:
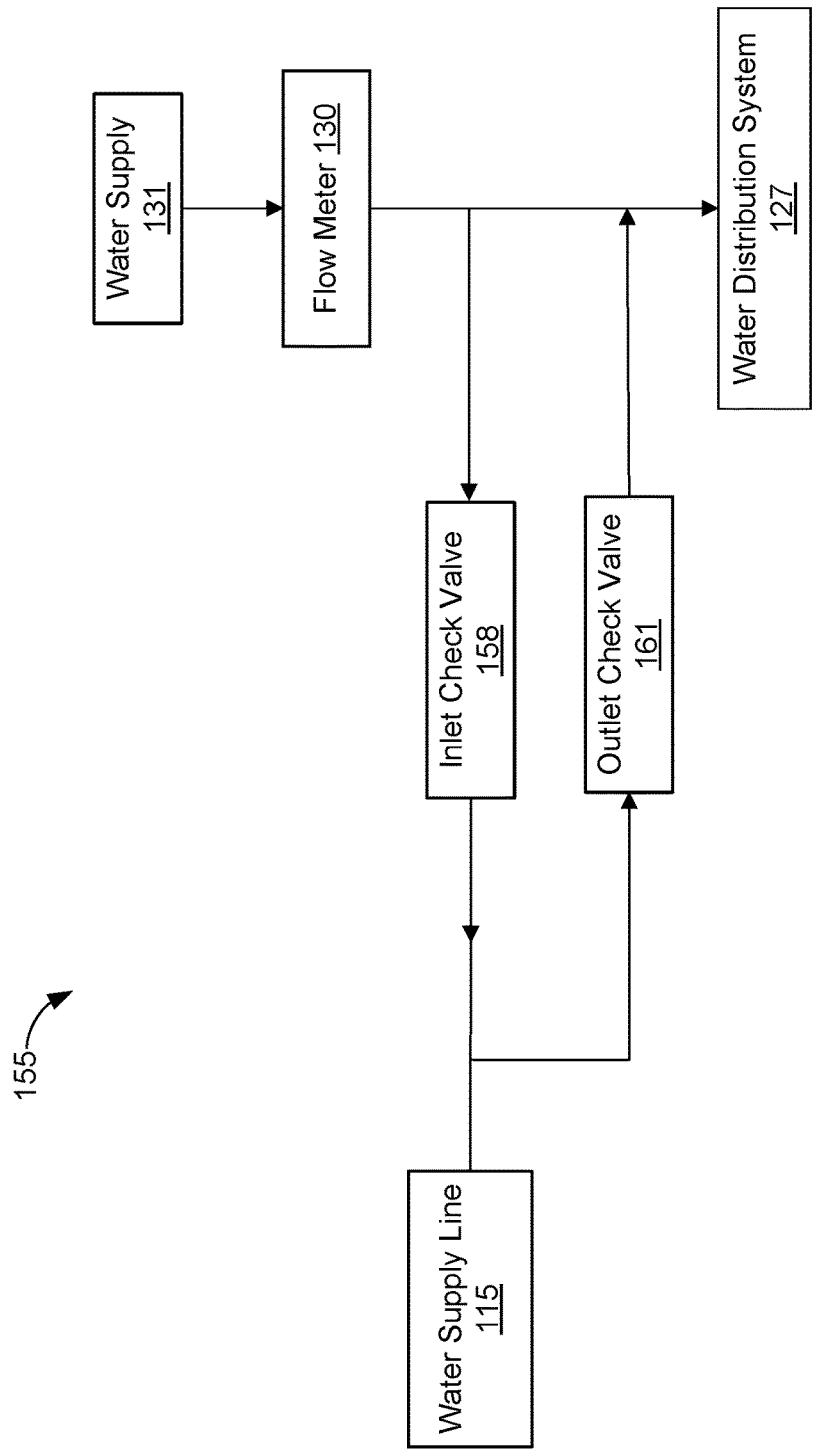
FIG. 1C illustrate an alternative water piping network for the water supply line in FIG. 1A according to one embodiment described herein.
Figure 2A:
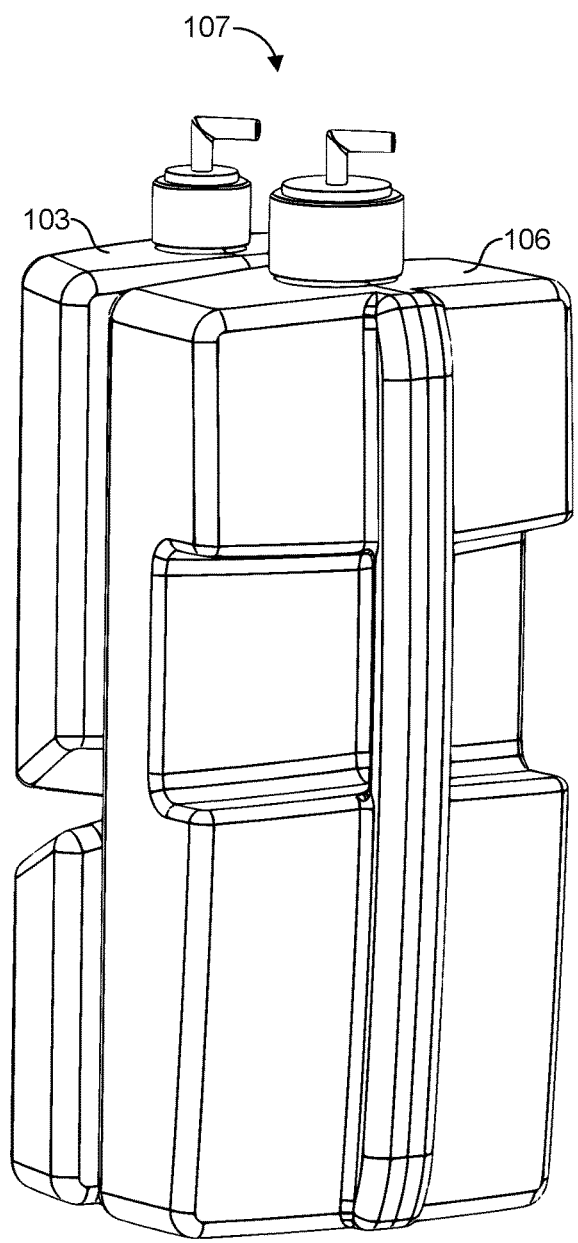
FIGS. 2A and 2B illustrate a perspective view and a cross-sectional view of a dosage container according to one embodiment described herein.
Figure 2B:
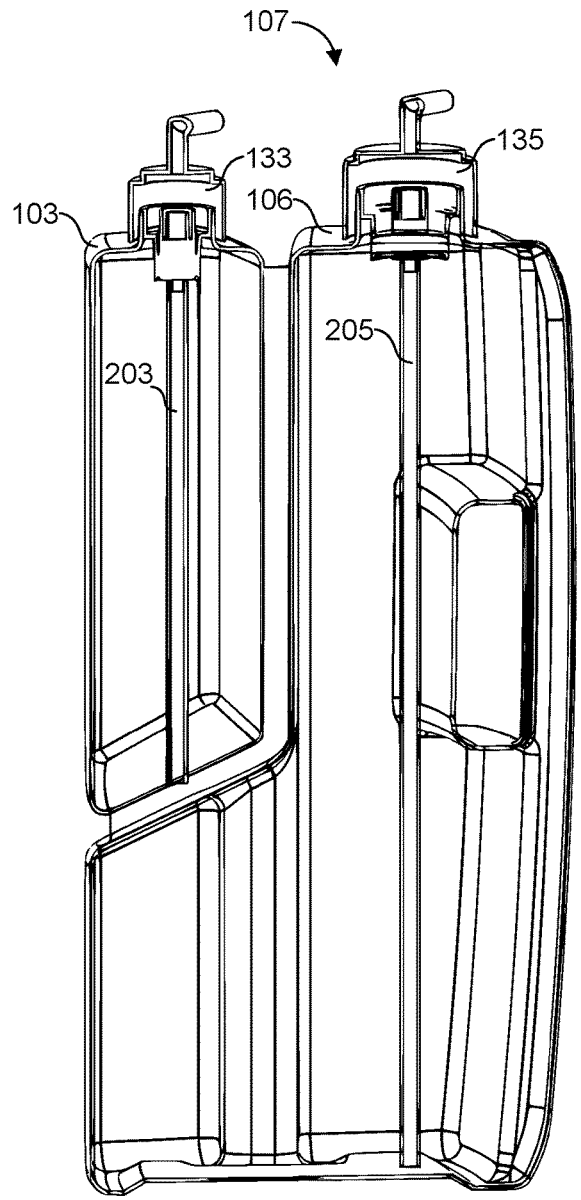

Turning to FIG. 1B, shown is a drawing of the components of the system 100 within an enclosure 147. As shown, the nutrient container 103 and the spores container 106 are part of the dosage container 107. The nutrient container 103 is connected to the adjustable valve 112 by way of a first tube 149*a*. The first tube 149*a* attaches to a first port 150*a* of the adjustable valve 112. The spores container 106 is connected to the adjustable valve 112 by way of a second tube 149*b*. The second tube 149*b* attaches to a second port 150*b* of the adjustable valve 112. The water supply line 115 is connected to a third port 150*c* of the adjustable valve 112 on one end. On the other end, the water supply line 115 may connect to an enclosure port 152 that leads outside of the enclosure 147, which in turns connects to the water distribution system 127 and the water source 124 (FIG. 1A). A third tube 149*c* connects the adjustable valve 112 and the syringe pump 109, where the third tube 149*c* is attached to a fourth port 153 of the adjustable valve 112. The first port 150*a*, the second port 150*b*, the third port 150*c*, the fourth port 153, and the enclosure port 152 may include a press-to-connect connection, a threaded connection, a compression connection, a flared connection, a barbed connection, and other suitable fluid connection fittings for fluid flow as can be appreciated. Additionally, FIG. 1B illustrates that the syringe pump 109 includes a tank 156 for receiving the spores, the nutrients, and the water. The syringe pump 109 may include a thermocouple 151 as part of the heater 141 and a brace 157 that attaches the syringe pump 109 to the enclosure 147. In other embodiments, the thermocouple 151 may be separate from the heater 141. In another embodiment, the system 100 includes a first thermocouple 151 as part of the heater 141 for measuring a temperature of the heater 141 and/or a second thermocouple 151 for measuring a temperature of the contents of tank 156 (e.g. water, dosage mixture, etc.).

As described herein, the controller 118 directs the system 100 through multiple phases of operation. As an example, the controller 118 can direct the system 100 through a sequence of drawing, heating, cooling, expelling, purging, and rinsing phases of operation, among others. In some embodiments, the execution of a sequence of the phases for providing a mixture of the spores, nutrients, and water into the water distribution system 127 can be referred to as a dosage cycle.

As a non-limiting example, the dosage cycle can begin in a neutral phase. In the neutral phase, the first port 150*a*, the second port 150*b*, and the third port 150*c* (collectively the "ports 150") of the adjustable valve 112 are closed off to the fourth port 153 of the adjustable valve 112, which provides access to the syringe pump 109. The controller 118 may detect the neutral position of the adjustable valve 112 from sensor data provided by the position sensor 146 (FIG. 1A).

If a vacuum phase is required, the controller 118 can cause the syringe pump 109 to create a vacuum in the tank 156 and the third tube 149*c* to account for the water pressure within the interior of the adjustable valve 112. The syringe pump 109 can create a vacuum by raising a plunger of the syringe pump 109 up from one end of the syringe pump 109.

In a drawing phase, the controller 118 can control the adjustable valve 112 to open individual channels to draw a volume of spores, a volume of nutrients, and a volume of water into the tank 156 of the syringe pump 109. The controller 118 can execute a sequence for drawing from each source individually according to an animal profile and/or a dosage plan. For example, the dosage profile for chickens can cause the adjustable valve 112 to first open a channel from the syringe pump 109 to the spores container 106 via the second tube 149*b*. For the illustrated embodiment, the adjustable valve 112 is a rotary valve. Thus, an aspect of the adjustable valve 112 rotates to open a channel between the syringe pump 109 and the second tube 149*b* for the spores container 106. At this point, the syringe pump 109 can draw a volume of spores from the spores container 106, through the second tube 149*b*, and into the adjustable valve 112. The volume of spores is then routed through the third tube 149*c* and into the tank 156 of the syringe pump 109. The adjustable valve 112 can then be rotated to open a channel from the syringe pump 109 to the nutrient container 103, which also closes the previous channel to the spores container 106. The syringe pump 109 can then draw a volume of spores solution into the tank 156. Next, the adjustable valve 112 can be rotated to open a channel between the syringe pump 109 to the water supply line 115. At this point, the syringe pump 109 can draw into the tank 156 a volume of water from the water supply line 115 and through the adjustable valve 112.

Another animal profile may have a different sequence. For instance, a cattle profile may call for the controller 118 to draw the water as a first step, the spores as a second step, and the nutrients as the third step. The collection of the volume of spores, the volume of nutrients, and the volume of water in the tank 156 can be referred to as a dosage mixture.

In a spore activation phase, the dosage mixture in the tank 156 can be heated to a temperature for a period of time. The dosage mixture is heated to activate the spores and induce germination. As shown in FIG. 1B, the heater 141 is wrapped substantially around the tank 156. The thermocouple 151 provides a temperature measurement to the controller 118. The controller 118 can instruct the heater 141 to heat the dosage mixture in a temperature range between 30 and 50 degrees Celsius. In some cases, the temperature range may be lower or higher depending upon the desired results.

Next, in a cooling phase, the dosage mixture in the tank 156 can be cooled down from the elevated temperature. The controller 118 can cause the syringe pump 109 to draw in additional water from the water supply line 115. In some scenarios with the additional water, the tank 156 may be substantially full. The dosage mixture can be allowed to sit in the tank 156 for a period of time. The additional water helps lower the temperature of the dosage mixture.

In an expelling phase, the controller 118 can cause the syringe pump 109 to expel the dosage mixture from the tank 156 through the third tube 149*c*. The dosage mixture is then routed through the adjustable valve 112, through the water supply line 115, and out of the enclosure 147 to the water distribution system 127. In another embodiment, the adjustable valve 112 may have an inlet water port that supplies water from the water supply 131 or the water source 124 to the adjustable valve 112. The adjustable valve 112 may also have an outlet water port that expels water or a dosage mixture from the adjustable valve 112 to the water distribution system 127. Thus, instead of a single port (i.e. third port 150*c*) that is used both for drawing water from the water source 124 and expelling a dosage mixture to the water distribution system 127, this embodiment may include two separate ports. The inlet water port and the outlet water port may be similar in shape and capability to the other ports 150 shown in FIGS. 1B, 4A, 4B, 4C, 4D, 4E, and 4F.

In a rinsing phase, the controller 118 can cause the system 100 to fill the tank 156 and the tubes 149*a*, 149*b*, 149*c* with water for the purpose of cleaning out remaining solution from the dosage mixture. During the rinsing phase, the syringe pump 109 can be used to draw enough water into the tank 156 until it is substantially full.

Then, in a purging phase, the controller 118 can cause the syringe pump 109 to purge the water from the tank 156 into the water supply line 115 and out the enclosure 147. Effectively, the rinsing phase and the purging phase are used to clean out the remaining dosage mixture in the tank 156 and the tubes 149*a*, 149*b*, and 149*c*, which prepare the system 100 for the next dosage cycle. As one skilled in the art can appreciate, the sequence of the phases can be altered. In another scenario, the dosage sequence may cause the controller 118 to first draw the water into the tank 156. Then, the controller 118 can cause the heater 141 to heat the water to a temperature between 80 and 95 degrees Celsius. The water is heated to kill bacteria in the water, which may at least partially sanitize the water. Then, the water may be allowed to cool to a temperature suitable for spore activation. Next, the controller 118 may draw into the tank 156 the volume of spores and nutrients. The controller 118 can cause the heater 141 to maintain the activation temperature for a period of time for the mixture to initiate an activation of the spores.

Moving on to FIG. 1C, shown is an alternative water piping network 155 for the water supply line 115 in FIG. 1A. In one exemplary scenario, the alternative water piping network 155 may be used when there is a long distance (e.g. more than ten feet) to the water source 124. In FIG. 1C, the alternative water piping network comprises an inlet check valve 158 for incoming water and an outlet check valve 161 for outgoing water. The check valves 158, 161 may allow for fluid flow in one direction. As water flows from the water supply 131, the system 100 (FIGS. 1A and 1B) may draw water from the water supply line 115. The drawing action by the system 100 can pull water from the water supply 131 through the inlet check valve 158 and into the water supply line 115, which routes the water to the adjustable valve (FIGS. 1A and 1B). Accordingly, when the system 100 is expelling water or a dosage mixture to the water distribution system 127, fluid flow is blocked at the inlet check valve 158 and may be forced to flow through a line for the outlet check valve 161 and into the water distribution system 127. Likewise, during a drawing phase, the outlet check valve 158 prevents fluid located passed the outlet check valve 158 from being drawn into the water supply line 115. Thus, expelled water or dosage mixture from a previous cycle will not be drawn into the water supply line 115.

Alternatively, the adjustable valve 112 may have a separate inlet port that supplies water from the water supply 131 or the water source 124 to the adjustable valve 112. The adjustable valve 112 may also have a separate outlet port that expels water or a dosage mixture from the adjustable valve 112 to the water distribution system 127. Thus, in some scenarios, the water can be expelled through the separate outlet port.

Next, FIG. 2A illustrates a dosage container 107, which includes the nutrient container 103 and the spores container 106 for the mixing system 100 shown in FIG. 1A and FIG. 1B. FIG. 2A illustrates a perspective view of the nutrient container 103 and the spore container 106, and FIG. 2B illustrates a cross-sectional view of the containers 103, 105.

As shown, the nutrient container 103 and the spore container 106 are embodied as two-part semi-rigid containers formed from plastic materials. In other embodiments, the containers 103 and 106 can be formed from different materials, have different shapes, be formed at different sizes, etc. The container 103 and 106 can be formed from injection molding, roto molding, blow molding, and other suitable molding techniques. The materials of the containers 103 and 106 may include linear low-density polyethylene (LLDPE), low-density polyethylene (LDPE), Polyethylene (PE), high density Polyethylene (HDPE), Polypropylene (PP), and other suitable materials for forming a container.

The nutrient container 103 includes a vent cap 133 having a filter, as described herein, to allow air in but to prevent particles from entering the nutrient container 103 as the contents of the nutrient container 103 are drawn out through the straw 203. Similarly, the spores container 106 includes a vent cap 135 having a filter to allow air in but to prevent particles from entering the spores container 106 as the contents of the spores container 106 are drawn out through the straw 206.

The vent caps 133 and 135 fit into the necks of the nutrient container 103 and the spores container 106 and can serve as a type of containment lock to prevent the nutrients and the spores from spilling. When the nutrient container 103 and the spores container 106 are not in use, a spring-loaded valve in the vent caps 133 and 135 can be held closed and a breathable membrane or filter allows gasses to pass through it, relieving any positive or negative pressure in the containers. As one example, the vent caps 133 and 135 can be embodied as SafTflo® inserts manufactured by RD Industries, Inc. of Omaha, Nebr., although similar inserts, caps, and vents can be relied upon.

Next, referring between FIGS. 3A and 3B, shown are different views of the syringe pump 109 in FIG. 1B. FIG. 3A shows an exploded view of the syringe pump 109 from FIG. 1B, and FIG. 3B illustrates a cross-sectional view of the syringe pump 109 from FIG. 1B. FIG. 3A illustrates that the syringe pump 109 comprises a pump motor 138, a cover 303, a shaft 306, a plunger 309, a brace 157, a tank 156, a heater 141, a base 312, a thermocouple 151, and a syringe port 315.

The pump motor 138 is positioned on top of the cover 303, and the cover 303 is placed on a first end of the tank 156. The pump motor 138 may have a threaded connection with the shaft 306. The pump motor 138 may also use two or more fasteners (e.g. screws) to connect with the cover 303. The shaft 306 is inserted through an aperture of the cover 303. The shaft 306 is also attached to the plunger 309 at a distal end.

The tank 156 has a cylindrical shape with an opening at each end. The tank 156 may be configured in other shapes as one skilled in the art can appreciate. The syringe pump 109 and/or the tank 156 may be comprised of materials such as stainless steel and other suitable metals. The syringe pump 109 and/or the tank 156 may also be comprised of material such as acrylonitrile butadiene styrene (ABS), polyvinyl chloride (PVC), polypropylene (PP), chlorinated polyvinyl chloride (CPVC), noryl polycarbonate, polyoxymethylene (POM), and other suitable plastic materials. The syringe pump 109 and/or the tank 156 may be constructed using a welded process, an extruded process, a rolled process, an injection molded process, a machined process, and other suitable manufacturing processes. The shaft 306 and the plunger 309 are inserted into one end of the tank 156.

At a second end, the tank 156 is attached to the base 312. The base 312 may be comprised of materials such as stainless steel and other suitable metals. The base 312 may also be comprised of material such as ABS, PVC, PP, CPVC, noryl polycarbonate, POM, and other suitable plastic materials. The base 312 may be constructed using an injection molded process, a machined process, and other suitable manufacturing processes.

The heater 141 and the brace 157 are wrapped substantially around the tank 156. The brace 157 may be used to attach the syringe pump 109 to a wall of the enclosure 147 (FIG. 1B). Other attachment structures may be used to attach the syringe pump 109 to the enclosure 147 as can be appreciated by one skilled in the arts. The thermocouple 151 may be inserted into the base 312. The syringe port 315 can be inserted into an aperture in the base 312. The syringe port 315 and thermocouple 151 may be connected to the base 312 via a press-to-connect connection, a threaded connection, a compression connection, a flared connection, a barbed connection, a flange and gasket connection, and other suitable fluid connection fittings for fluid flow as can be appreciated.

The pump motor 138 has a threaded engagement with the shaft 306. The shaft 306 can have a threaded outer surface to engage with the pump motor 138. The pump motor 138 comprises a top aperture and a bottom aperture. The shaft 306 is inserted through the top aperture and the bottom aperture. Thus, the pump motor 138 can be used to pull and push the shaft 306 along its length via the threaded engagement. As a result, the plunger 309 can be raised and lowered within the tank 156 as the shaft 306 is mechanically controlled by the pump motor 138.

The base 312 comprises a proximity sensor to detect that the position of the plunger 309 within the tank 156. In some embodiments, the proximity sensor may be a hall effect sensor, a reed switch, a capacitive switch, a miroswitch, a contact switch, and other suitable proximity sensors. In some scenarios, the proximity sensor provides an indication to the controller 118 at an instance in which the plunger 309 is substantially adjacent to the base 312, as depicted in FIG. 3B. In other scenarios, the proximity sensor provides data indicating a current distance of the plunger 309 from the base 312. In some examples, the proximity sensor is omitted. Instead, the controller 118 may detect that the plunger 309 has contacted the base 312 or the cover 303 because the plunger 309 cannot advance beyond its current position. In another example, a portion of the plunger 309 may contact a position switch near the cover 303 or the base 312. Once contacted by a portion of the plunger 309, the position switch can trigger a signal to the controller 118. The signal can indicate to the controller 118 that the plunger 309 is near the cover 303 or the base 312. Additionally, FIG. 3B can also represent the plunger 309 in the neutral phase or a default position.

The cover 303 has air vents that allow air to escape as the plunger 309 is raised and lowered within the tank 156. The air vents may also include a filter that prevent containments from entering the tank 156. In some embodiments, the air vents may be omitted. The cover 303 may be comprised of materials such as stainless steel and other suitable metals. The cover 303 may also be comprised of material such as ABS, PVC, PP, CPVC, noryl polycarbonate, POM, and other suitable plastic materials. The cover 303 may be constructed using an injection molded process, a machined process, and other suitable manufacturing processes.

The plunger 309 comprises multiple ribs that contact the interior wall of the tank 156. The ribs can facilitate creating a seal against the interior wall of the tank 156. The ribs can also facilitate cleaning the interior wall of the tank 156 during the rinsing and purging phases of operations. The plunger 309 may also include an annular cavity 313 that provides space for a protruding portion of the thermocouple 151, as illustrated in FIG. 3B. The annular cavity 313 surrounds a central extended portion of the plunger 309. In some embodiments, the syringe pump 109 may have two thermocouples 151. A first thermocouple 151 may be inserted through the base 312 for detecting a temperature of a fluid in the tank 156, as illustrated in FIG. 3B. A second thermocouple 151 may be embedded as part of the heater 141 and is used to provide a temperature of the heater 141.

Turning to FIGS. 3C and 3D, shown are different positions of the plunger 309 within the tank 156 of the syringe pump 109. In one scenario, FIG. 3C can illustrate a position of the plunger 309 in a vacuum phase. In the vacuum phase, the plunger 309 can be pulled upward toward the cover 303 to create a vacuum within the syringe pump 109, which can facilitate relieving water pressure in the adjustable valve 112 (FIG. 1B). If the vacuum phase is not required, the FIG. 3C may represent drawing nutrients, spores, and/or water into the tank 156. The plunger 309 can be pulled further toward the cover 303 during the dosage stage. For example, after a channel to the water supply line 115 has been opened, the pump motor 138 can draw a volume of water into the tank 159 by pulling the plunger 309 up toward the cover 303 by a first distance. Then, a channel to the spores container 106 is opened, and the pump motor 138 can draw a volume of spores into the tank 159 by puffing the plunger 309 up toward the cover 303 by a second distance.

FIG. 3D illustrates the shaft 306 has been pulled to such an extent that the plunger 309 is adjacent the cover 303. FIG. 3D may represent a state where the tank 156 is substantially full with a dosage mixture or water. FIG. 3D may represent the system 100 is in a drawing phrase. Alternatively, FIG. 3D may represent the system 100 is in a rinsing or purging phrase. FIG. 3D also illustrates that a portion of the shaft 306 extends out of the top aperture of the pump motor 138. If less water is desired, the plunger 309 does not reach the top of the tank 156 and contact the cover 303.

Turning to FIG. 4A, shown is a front view of the adjustable valve 112. As shown, the adjustable valve 112 is a rotary valve. FIG. 4A also includes a cross-sectional reference "AA" for FIGS. 4C through 4F. In FIG. 4A, the valve motor 143 comprises an axil 403 that attaches to an interior chamber 416 of the adjustable valve 112. The valve motor 143 comprises a motor 411 and a gear box 412. FIG. 4B shows is an exploded view of the adjustable valve 112 in FIG. 4A. The adjustable valve 112 includes a valve motor 143 that may be attached to pillars 404*a*, 404*b* (collectively pillars 404). Although not shown, the adjustable valve 112 has four pillars 404 in the illustrated embodiment. The pillars 404 are attached to a support plate 407. The support plate 407 has an aperture in which the axil 403 of the valve motor 143 is inserted. The axil 403 is attached to a valve drive 410 via a motor coupler 414. The valve drive 410 is in turn is connected to the interior chamber 416. The interior chamber 416 is positioned inside of a valve housing 419. The mounting bracket 422 can be attached to a wall of the enclosure 147 (FIG. 1B).

The valve housing 419 is attached to the first port 150*a*, second port 150*b*, third port 150*c*, and the fourth port 153. The interior chamber 416 is configured to rotate within the valve housing 419. As the axil 403 of the valve motor 143 turns, the valve drive 410 also turns the interior chamber 416. The rotation of the interior chamber 416 opens and closes channels to the nutrient container 103, the spores container 106, and the water supply line (FIG. 1A).

Referring between FIGS. 4C through 4F, shown is an exemplary progression of the interior chamber 416 rotating within the valve housing 419. FIGS. 4C through 4F are cross-sectional views of the adjustable valve 112 in FIG. 4A with respect to the cross-sectional reference AA. FIG. 4C illustrates the adjustable valve 112 in the neutral position. As shown, the interior chamber 416 has an elbow channel 425 that connects to the fourth port 153 (FIG. 4B) on a first end. The second end 428 of the elbow channel 425 can be aligned with one of the first port 150*a*, second port 150*b*, and the third port 150*c*. As shown, the elbow channel 425 is not connected to any of the ports 153 because it is facing the interior wall of the valve housing 419. Thus, all ports 153 are dosed off to the syringe pump 109. In some embodiments, a neutral state refers to an orientation when all ports 153 are closed off to the syringe pump 109.

FIG. 4D illustrates that the second end 428 of the elbow channel 425 has been rotated to align with the third port 150*c*. The second end 428 of the elbow channel 425 rotates as the interior chamber 416 rotates within the valve housing 419. In this orientation, the syringe pump 109 is connected to the water supply line 115 (FIG. 1B). Thus, there is a channel for the syringe pump 109 to draw water from the water supply line 115 and into the syringe pump 109. The channel comprises a path from the water supply line 115 through the third port 150*c* and into the adjustable valve 112 (FIG. 1B). The path continues through the second end 428 of the elbow channel 425 and through the fourth port 153 of the adjustable valve 112. From there, the path continues from the fourth port 153 through the third tube 149*c* and into the tank 156.

In FIG. 4E, the second end 428 of the elbow channel 425 has been rotated and aligned with the first port 150*a*, which also doses the channel to the third port 150*c*. In this orientation, the syringe pump 109 is connected to the nutrient container 103 (FIGS. 1A, 1B). Thus, there is a channel for the syringe pump 109 to draw a volume of solution from the nutrient container 103 and into the syringe pump 109 (FIG. 1B). The channel comprises a path from the nutrients container 103 through the first tube 149*a*, through the first port 150*a*, and into the adjustable valve 112 (FIG. 1B). The path continues through the second end 428 of the elbow channel 425 and through the fourth port 153 of the adjustable valve 112. The path continues from the fourth port 153 through the third tube 149*c* and into the tank 156.

In FIG. 4F, the second end of the elbow channel 425 has been rotated and aligned with the second port 150*b*, which also closes the channel to the first port 150*a*. In this orientation, the syringe pump 109 is connected to the spores container 106 (FIGS. 1A, 1B). Thus, there is a channel for the syringe pump 109 to draw a volume of solution from the spores container 106 and into the syringe pump 109. The channel comprises a path from the spores container 106 through the second tube 149*b*, through the second port 150*b*, and into the adjustable valve 112 (FIG. 1B). The path continues through the second end 428 of the elbow channel 425 and through the fourth port 153 of the adjustable valve 112. The path continues from the fourth port 153 through the third tube 149*c* and into the tank 156.

In another embodiment, the adjustable valve 112 may have a fifth port, which may be opposite of the first 150*a*. The fifth port 150 may be used to allow for a separate inlet port and outlet port to the enclosure 147 (FIG. 1B). In this example, the fifth port may be used as an inlet port for incoming water from the water source 124 (FIG. 1A).

Incoming water would flow through the fifth port in order to enter the adjustable valve 112. Then, the third port 150c may be used an outlet port for expelling water or a dosage mixture from the adjustable valve 112 to the water distribution system 127 (FIG. 1A).

Figure 4A:
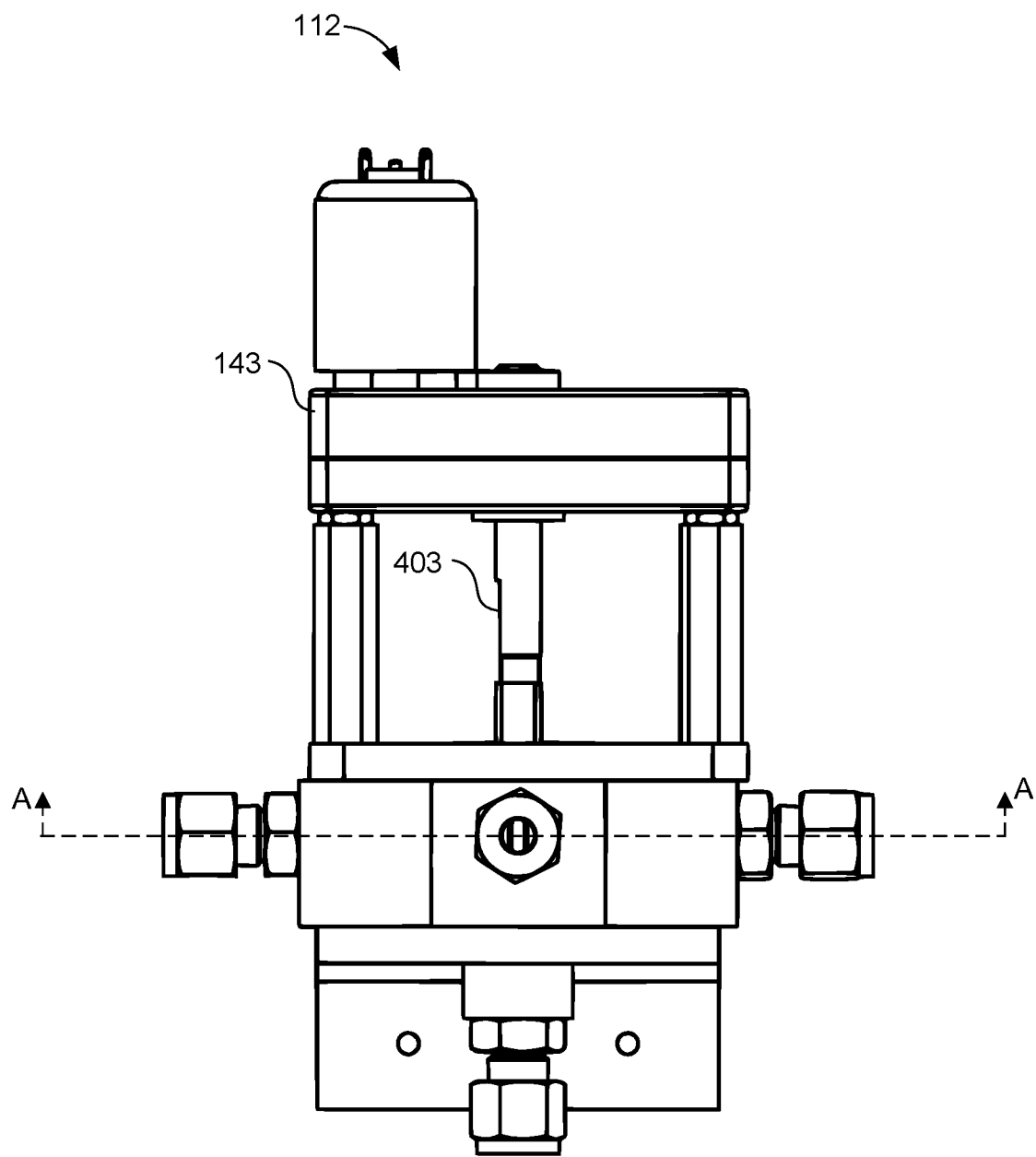
FIGS. 4A through 4F illustrate various views of an adjustable valve according to various embodiments of the present disclosure.
Figure 4B:
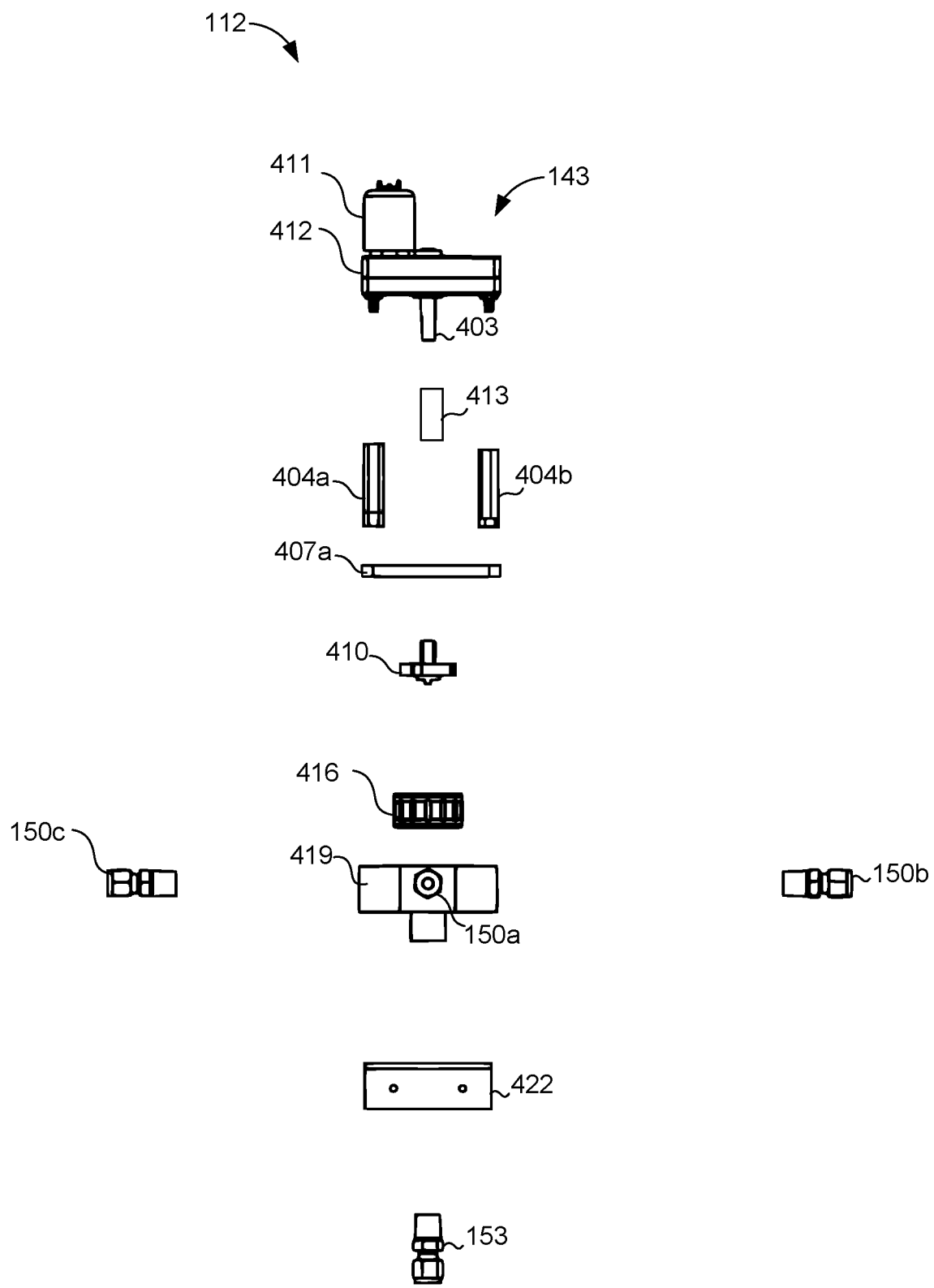
Figure 4G:
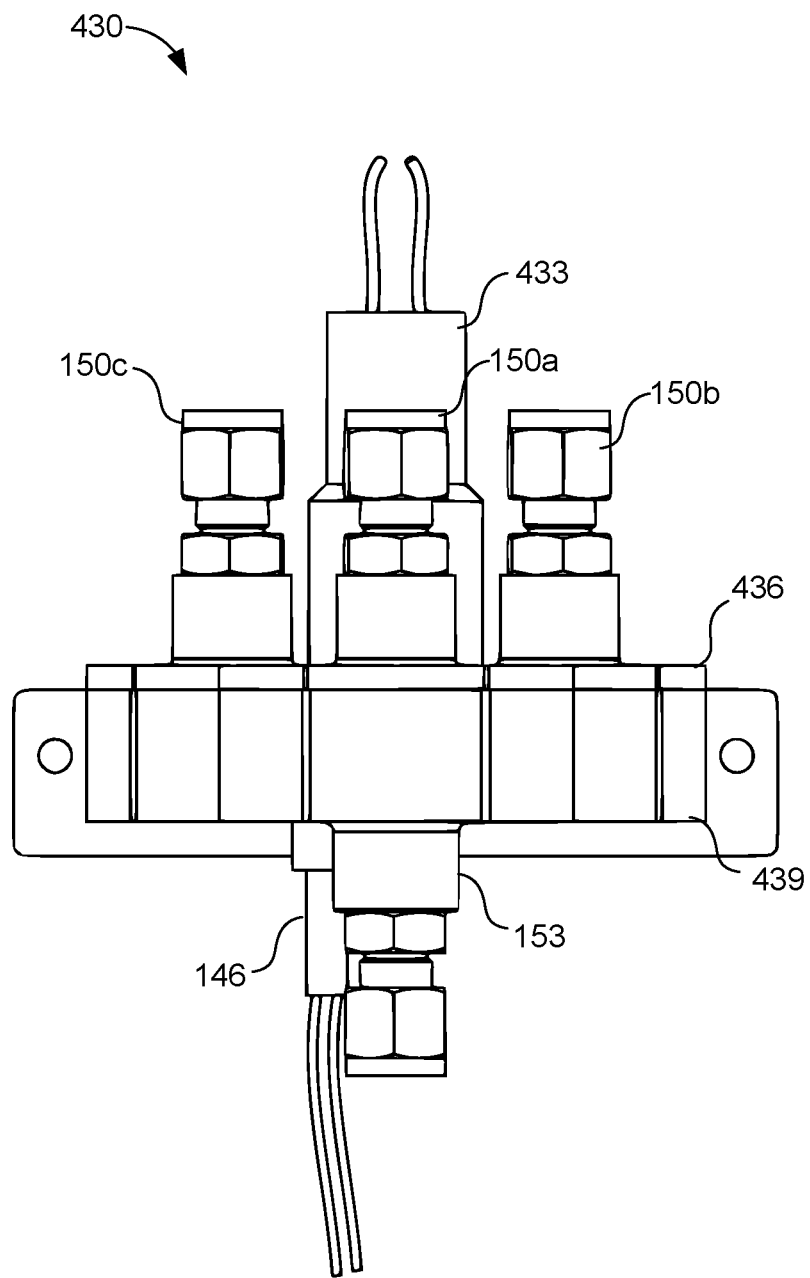
FIGS. 4G though 4S illustrate various views of an alternative adjustable valve according to various embodiments of the present disclosure.

Turning to FIGS. 4G through 4S, shown are various views of an alternative adjustable valve 430. FIG. 4G illustrates a front view of the alternative adjustable valve 430. The alternative adjustable valve 430 may comprise the first port 150a, the second port 150b, the third port 150c, and the fourth port 153 similar to the adjustable valve 112. The ports 150a, 150b, 150c, and 153 may have similar tube connections as shown in FIG. 1B. In FIG. 4G, the alternative adjustable valve 430 may also comprise a motor 433, a valve cover 436, a valve base 439, and a position sensor 146.

Figure 4H:
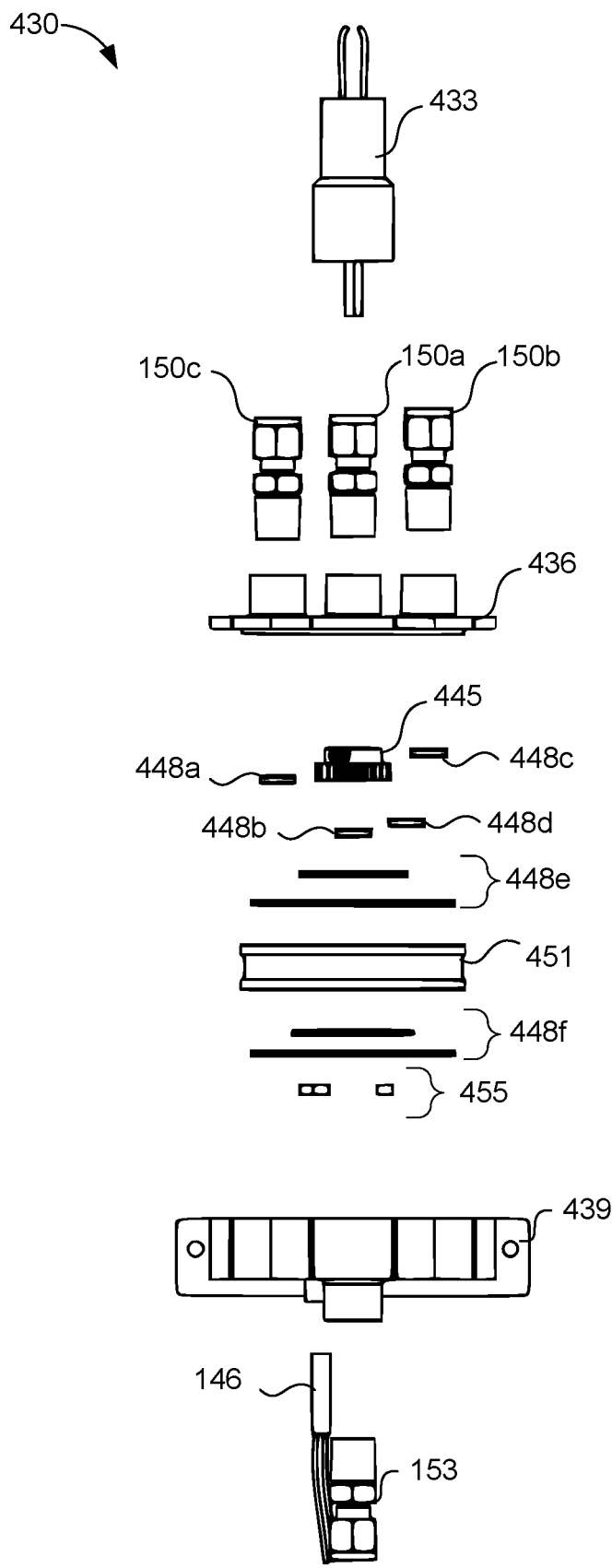

Moving to FIG. 4H, shown is an exploded view of the alternative adjustable valve 430 in FIG. 4G. FIG. 4H illustrates that the alternative adjustable valve 430 also may comprise a locking gear 445, o-rings 448a-448f, a valve core 451, and one or more magnets 455. FIG. 4H illustrates that the motor 433 connects to and through the valve cover 436. The motor 433 also connects to the locking gear 445, which may be positioned inside of the valve core 451. The locking gear 445 may be a spur gear, a hex-shaped gear, and other suitable shapes that can be used for engaging the motor 433. The valve core 451 sits inside of the valve base 439. The ports 150a-c connect to the valve cover 436. O-rings 448a-d may be positioned on the underside of the valve cover 436 at apertures aligned with the ports 150a-c. O-rings 448e and 448f can be positioned in annular grooves on a top side and a bottom side of the valve core 451. The o-rings 448a-f may be comprised of materials such as Silicone, ethylene propylene diene monomer rubber (EPDM), Santoprene, Viton, Buena, and other suitable materials. The o-rings 448a-f may be constructed using a compression process, an injection molded process, an over mold process and other suitable manufacturing processes.

The magnets 455 may be positioned in position designations on the underside of the valve core 451. The position sensor 146 and the fourth port 153 may be attached to the valve base 439.

Figure 4I:
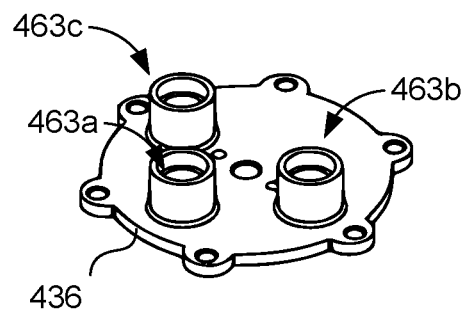
Figure 4J:
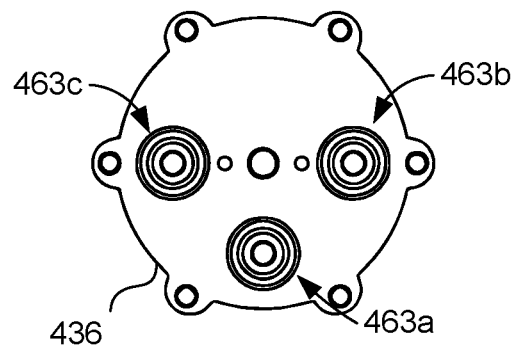
Figure 4K:
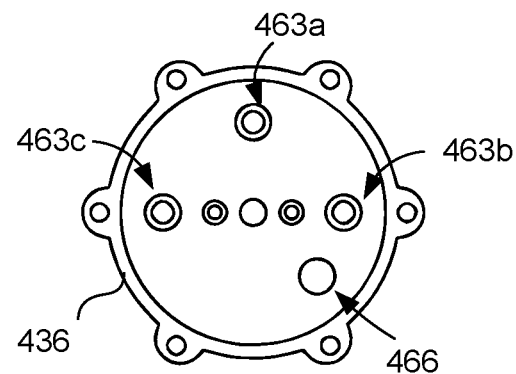

With reference to FIGS. 4I through 4K, shown are different views of the valve cover 436. FIG. 4I illustrates a top perspective view of the valve cover 436. FIG. 4J illustrates a top view of the valve cover 436. FIG. 4K illustrates a bottom view of the valve cover 436. The valve cover 436 may comprise cover apertures 463a-c, which are connected to ports 150a-c. FIG. 4K also illustrates that the bottom side of the valve cover 436 may comprise a closed position location 466.

Figure 4L:
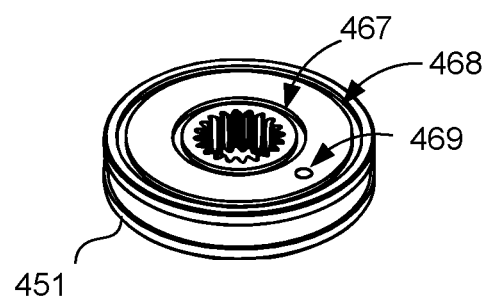
Figure 4M:
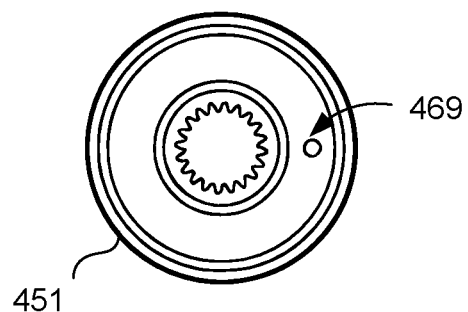
Figure 4N:
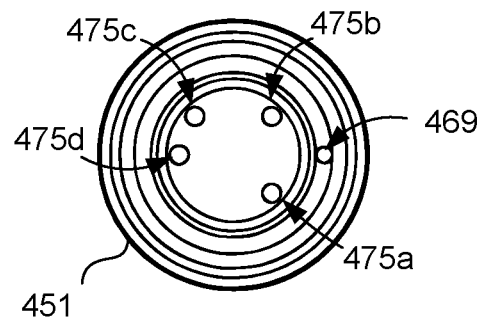

With reference to FIGS. 4L through 4N, shown are different views of the valve core 451. FIG. 4L illustrates a top perspective view of the valve core 451. FIG. 4L depicts that the valve core 451 may comprise an inner annular groove 467 and an outer annular groove 468. O-rings 448f can be positioned inside of the inner annular groove 467 and the outer annular groove 468. FIG. 4M illustrates a top view of the valve core 451. FIG. 4N illustrates a bottom view of the valve core 451.

The valve core 451 may comprises multiple ridges along an inner cavity of the valve core 451. The locking gear 445 may be positioned within the inner cavity of the valve core 451. The valve core 451 may comprise a channel aperture 469 that allows fluid to pass from one of the ports 150a-c to the fourth port 153. The channel aperture 469 rotates along the perimeter as the valve core 451 is rotated. Thus, the channel aperture 469 can align with one of the ports 150a-c.

When one of the port 150a-c are aligned with the channel aperture 469, a channel is opened from the aligned port 150 to the fourth port. All ports 150a-c may be closed when the channel aperture 469 is not aligned to any of the ports 150a-c, such as with the neutral position location 466 (FIG. 4K). The valve core 451 may also comprise position designations 475a-d. The position designations 475 can be placement locations for magnets 455 to determine the position or orientation on the alternative adjustable valve 430. The orientation or position may be used to determine which channel is opened to the fourth port 153 and/or which channels are closed to the fourth port 153. In some embodiments, the magnets 455 may be detected by the position sensor 146 (e.g. the reed switch). In one embodiment, between every two position designations 475a-d may be a different arcuate distance. The arcuate distance between position designations 475a-d can be used to identify a position of the valve core 451, which can indicate which ports 150a-c are opened and closed.

Figure 4O:
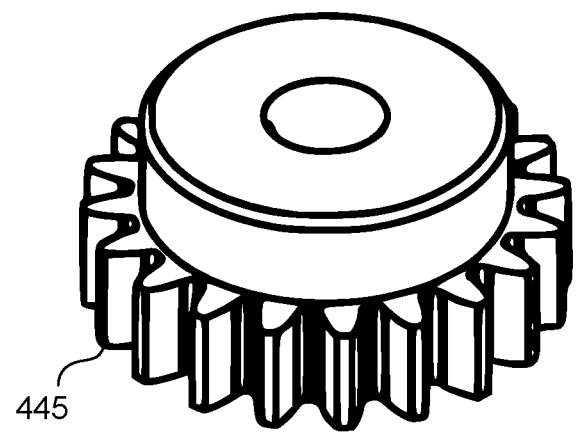

Turning to FIG. 4O, shown is a top perspective view of the locking gear 445. The locking gear 445 may include multiple ridges along its perimeter. The ridges of the locking gear 445 may be in contact with corresponding ridges of the valve core 451. The locking gear 445 may be positioned within the valve core 451. An axil of the motor 433 may attach within a center aperture of the locking gear 445. As the motor 433 turns the locking gear 445, the valve core 451 is rotated within the valve base 439. Additionally, the locking gear 445 may be replaced with any suitable key that locks the motor axis 403 and engages the valve core 451.

Figure 4Q:
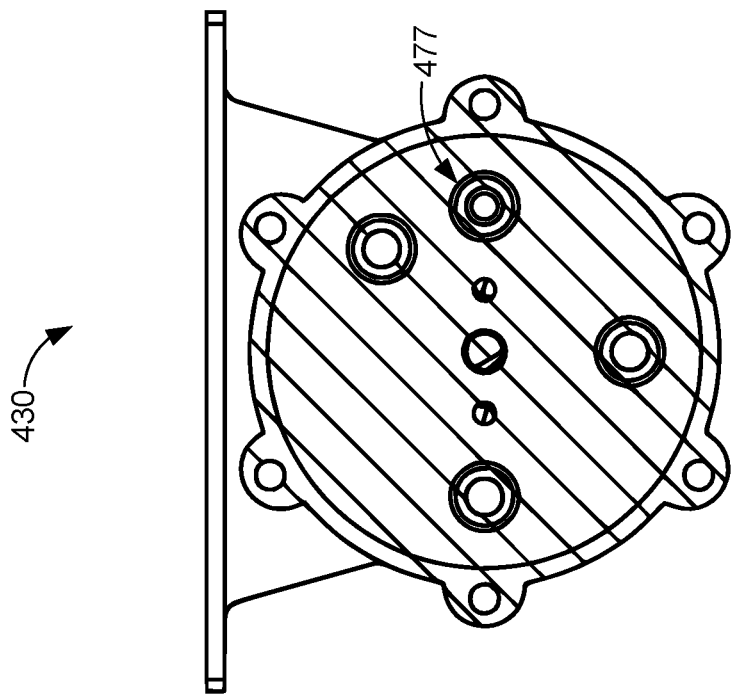
Figure 4P:
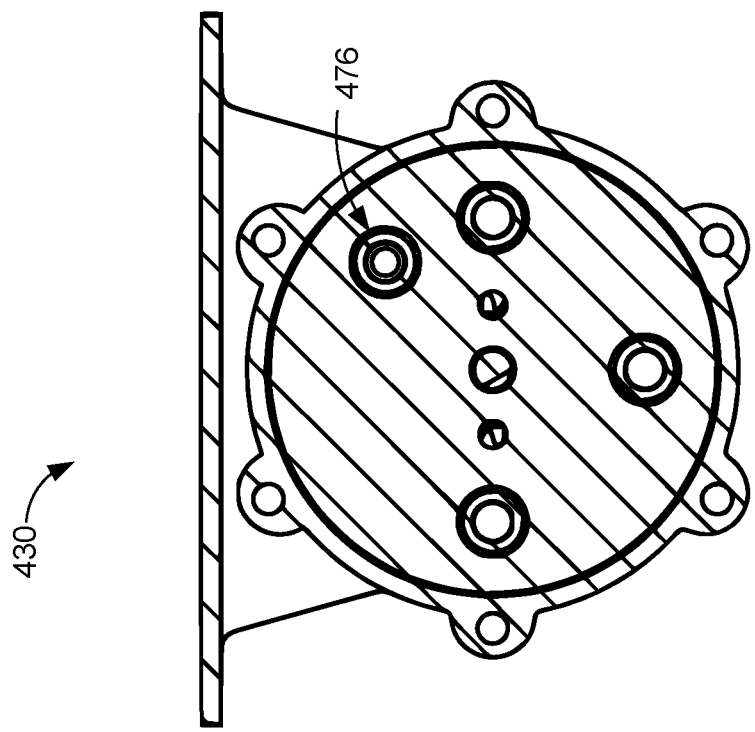

Moving to FIGS. 4P through 4S, shown are cross-sectional views of an exemplary progression of the alternative adjustable valve 430. FIG. 4P depicts a reference arrow 476 to illustrate the alternative adjustable valve 112 is in a closed position. The channel aperture 469 (FIG. 4M) is aligned to the neutral position location 466 (FIG. 4K) of the valve cover 436. In the neutral position, all of the ports 150a-c may be closed off to the fourth port 153. Thus, fluid, such as water or dosage mixtures, cannot flow through the alternative adjustable valve 430.

FIG. 4Q depicts a reference arrow 477 to illustrate the alternative adjustable valve 430 has an open channel to port 150b, which is connected to the spores container 106. Thus, a volume of spore can flow from the spores container 106 into port 150b and out of port 153 (FIG. 4G).

Figure 4S:
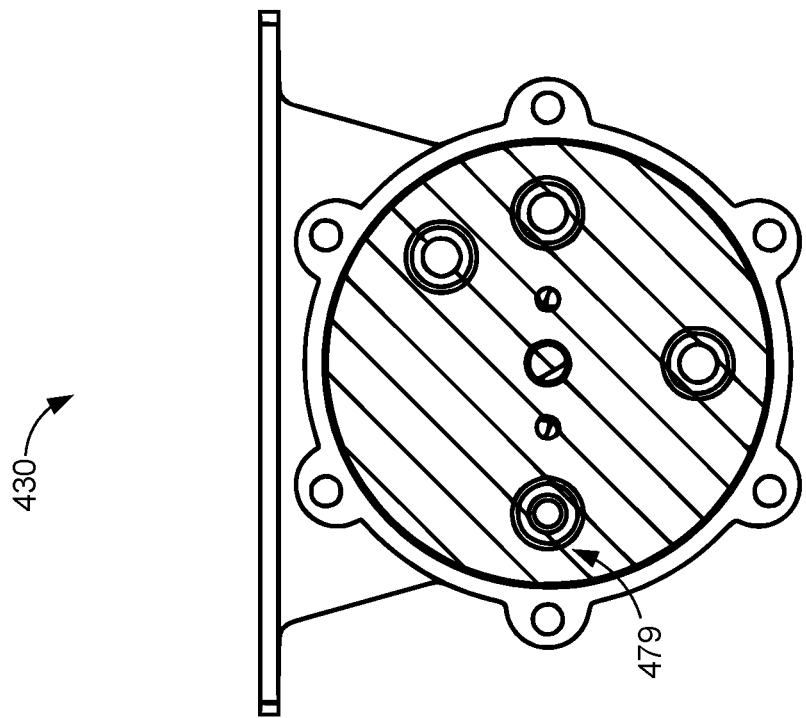
Figure 4R:
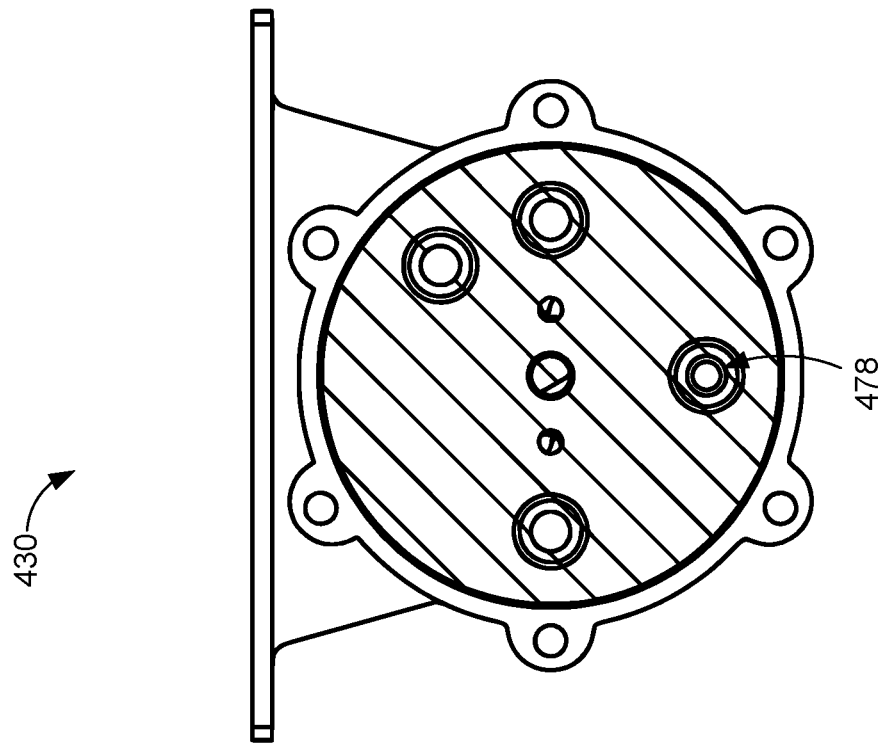

FIG. 4R depicts a reference arrow 478 to illustrate the alternative adjustable valve 112 has an open channel to port 150a, which is connected to the nutrient container 103. Thus, a volume of nutrient can flow from the nutrient container 103 into port 150a and out of port 153 (FIG. 4G).

FIG. 4S depicts a reference arrow 479 to illustrate the alternative adjustable valve 112 has an open channel to port 150c, which is connected to the water supply line 115. Thus, a volume of water can flow from the water supply line 115 (FIG. 1A) into port 150c and out of port 153 (FIG. 4G).

Referring next to FIG. 5, shown is a flowchart that provides one example of the operation of the controller 118 according to various embodiments. It is understood that the flowchart of FIG. 5 provides merely an example of the many different types of functional arrangements that may be employed to implement the operation of a portion of the controller 118 as described herein. As an alternative, the flowchart of FIG. 5 may be viewed as depicting an example of elements of a method implemented in the controller 118 (FIG. 1A) according to one or more embodiments.

Beginning with box 503, the controller 118 can detect a triggering condition to execute the system 100. Some non-limiting examples of triggering conditions may include a timer configured to initiate a dosage cycle on a periodic interval, on a schedule, animal activity, human activity, plant activity, water flow, an estimated drinking start time, an estimated peak drinking time, a drinking time based on a sunrise time, or on some other suitable basis. In other examples, the system 100 can initiate a dosage cycle in response to detection of animals in close proximity. Sensors may be used to detect the presence of one or more animals near a water distribution system 127 (FIG. 1B). In another example, the system 100 can initiate a dosage cycle according to water consumption profile for a location, a type of animal, or other suitable water conditions.

In box 506, the controller can detect that the adjustable valve 112 (FIG. 4C) is at a neutral position. In some embodiments, the neutral position refers to a position where the syringe pump 109 is closed off to the spores container 106, the nutrient container 103, and the water supply line 115. The neutral position can also indicate that the plunger 309 is adjacent to the base 312 (FIG. 3A). In the neutral position, the controller 118 can cause the syringe pump 109 to create a vacuum in the tank 156 and the tubes (e.g. the third tube 149c) leading to the adjustable valve 112.

In box 509, the controller 118 can draw a volume of spores solution into the tank 156 from the spores container 106 using the syringe pump 109 and the adjustable valve 112. In some embodiments, the controller 118 can cause the adjustable valve 112 to open a channel from the syringe pump 109 to the second port 150b. The adjustable valve 112 can move the elbow channel 425 to align with the second port 150b (FIG. 4F). Then, the controller 118 can cause the syringe pump 109 to draw a volume of the spores solution by operating the plunger 309.

In box 512, the controller 118 can draw a volume of nutrient solution into the tank 156 from the nutrient container 103 using the syringe pump 109 and the adjustable valve 112. In some embodiments, the controller 118 causes the adjustable valve 112 to actuate to open a channel from the syringe pump 109 to the first port 150a. The adjustable valve 112 moves the elbow channel 425 to align with the first port 150a (FIG. 4E). Then, the controller 118 can cause the syringe pump 109 to draw a volume of the spores solution by operating the plunger 309.

In box 515, the controller 118 can draw a volume of water into the tank 156 from the water supply line 115 using the syringe pump 109 and the adjustable valve 112. In some embodiments, the controller 118 causes the adjustable valve 112 to open a channel from the syringe pump 109 to the third port 150c. The adjustable valve 112 moves the elbow channel 425 to align with the third port 150c (FIG. 4D). Then, the controller 118 can cause the syringe pump 109 to draw a volume of the water by operating the plunger 309.

In box 518, the controller 118 can heat the mixture to a predefined temperature using the heater 141. In some embodiments, the heater 141 maintains the predefined temperature for a period of time in order to active the spores. In some scenarios, while the heater 141 is activated, the adjustable valve 112 may open or leave open a channel to the water supply line 115 in order to relief pressure that can build during the heating of the water or the dosage mixture. In some embodiments, the set temperature for the heater 141 may be adjusted based on a temperature of the water in the water supply line 115, the water source 124, an outdoor temperature, or some other temperature reading associated with the system 100. The heater 141 may be set to a higher temperature in order to shorten the amount of time needed to bring the temperature of the water or dosage mixture to a desired temperature. For example, during the winter months, the heater 141 can automatically adjust to a higher temperature based on incoming water temperature (e.g. water supply line 115, water source 124, and/or water supply 131). Thus, the adjusted temperature of the heater 141 may be higher in the winter months than the summer months in order to shorten the amount of time needed to get the temperature of the fluid in the tank 156 to an activation temperature. In some cases, an initial temperature measurement of the incoming water may be used to automatically determine a temperature setting for bringing the water or dosage mixture to a desire activation temperature within a particular period of time. For example, during the winter, the system 100 may detect an initial temperature measurement that is below a yearly average temperature or a low temperature threshold. The controller 118 may then automatically adjust the heater 141 to a higher temperature in order to bring the temperature of the water or dosage mixture to the desired temperature in a quicker period of time.

In box 521, the controller 118 can draw water into the tank 156 in order to cool down the heated mixture. The controller 118 controls the syringe pump 109 and the adjustable valve 112 to draw the water into the tank 156. The mixture may be allowed to cool for a period of time. Alternatively, in some embodiments, the controller 118 may wait until the mixture reaches a cooled down temperature threshold.

In box 524, the controller 118 can cause the syringe pump 109 to dispense the mixture through the adjustable valve 112 and through the water supply line 115. At this stage, the mixture can be dispensed into the water distribution system 127 for animal consumption, plant consumption, or human consumption.

In box 527, the controller 118 can draw water into the tank 156 from the water supply line 115. The water is drawn into the tank 156 in order to flush out any remaining mixture solution. In this phase, the syringe pump 109 can substantially fill the tank 156.

In box 530, the controller can expel the water from the tank 156 to the adjustable valve 112. From the adjustable valve 112, the water can be expelled through the water supply line 115 and out of the enclosure 147. In some embodiments, the adjustable valve 112 may have a separate inlet port and outlet port to the enclosure 147 (FIG. 1B). In this example, the water can be expelled through the separate outlet port.

Turning to FIG. 6, shown is a front view of an adjustable valve assembly 602 that can be operated by a controller 115 in the system 100. The adjustable valve assembly 602 includes a motor 605, an adjustable valve 608, and a mounting bracket 611. The motor 605 can cause the rotation of components of the adjustable valve assembly 602 in order to draw fluid into the tank 156 or expel fluid from the tank to the water distribution system 127.

Among other components, the adjustable valve 608 can include a motor mount 614, a valve base 617, port connections 620*a*, 620*b*, 620*c* (omitted from view), 620*d* (omitted from view) (collectively "the port connections 620"), a tank port connection 622, and a position sensor 623. The port connections 620 can be attached, via a tube 149, to a water supply line 115, a nutrient container 103, a spores container 106, or other suitable elements. The port connections 620 can also be used as a vent port for depressurizing the adjustable valve 608. Also, the tank port connection 622 can be attached to the tank 156, via a third tube 149*c*.

As the adjustable valve 608 is rotated, the adjustable valve 608 can align internally a fluid channel (FIG. 8) to one of the port connections 620. Once aligned, the fluid channel allows fluid to flow from the one of the port connections 620 to the tank port connection 622 or from the tank port connection 622 to one of the portion connections 620. The adjustable valve 604 can also orient the fluid channel to a home or off state to close off access to all of the port connections 620. The position sensor 623 can be used to sense the position of the adjustable valve 604 while it rotates. By sensing the position, a controller 118 can identify a position of internal components (e.g., the fluid channel) of the adjustable valve 604 with respect to the port connections 620. After knowing the position, the controller 118 can command the motor 605 to rotate the adjustable valve 604 a particular amount in order to align the internal components of the adjustable valve 604 to a certain orientation, such as in an off state or in a state of alignment with a particular port connection 620. For example, the controller 115 can instruct the motor 605 to rotate 90 degree in order to align the side opening of the valve core 631 with a port connection 620. The mounting bracket 611 can be used to attach the adjustable valve assembly 602 to a wall of the enclosure 147. The position sensor 623 can be a hall-effect sensor, a proximity sensor, or other suitable position sensor. In some contexts, the adjustable valve 608 can be considered as a rotatory valve as one non-limiting example.

Figure 7A:
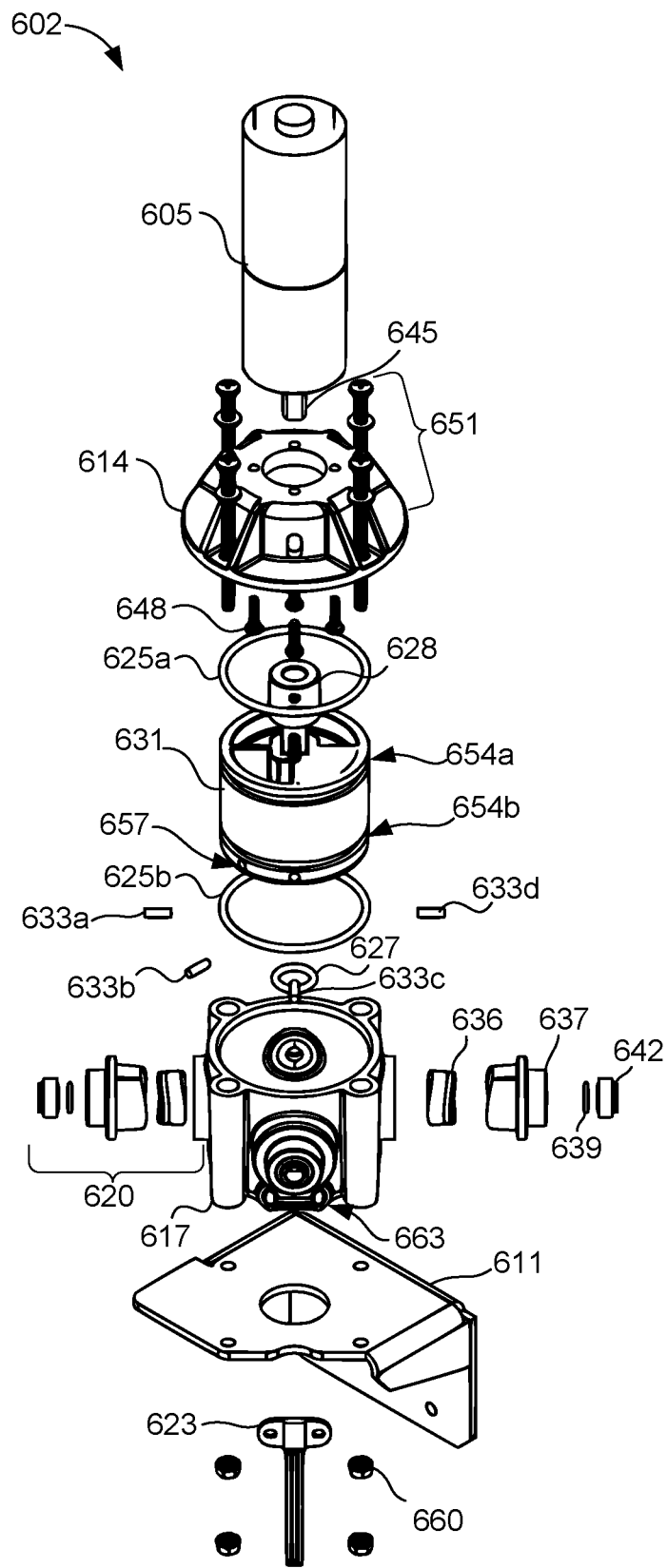

Moving on to FIG. 7A, shown is an exploded view of the adjustable valve assembly 602. Among other components, FIG. 7A illustrates that the adjustable valve assembly 602 can include a motor 605, the mounting bracket 611, a motor mount 614, the valve base 617, the port connections 620, the position sensor 623, a first core o-ring 625a, a second core-o-ring 625b (collectively "the core o-rings 625"), a base o-ring 627, a motor coupler 628, a valve core 631 magnets 633a-d (collectively "the magnets 633"), a gasket 636, a port o-ring 639, and a fitting 642.

The motor 605 can attach to the motor coupler 628. The motor 605 has a shaft 645 at a distal end. The shaft 645 can extend through a central opening of the motor mount 614 and attach to the motor coupler 628. The motor 605 can be attached to the motor mount 614 by one or more motor mount screws 648. The motor mount screws 648 can be inserted through openings in the motor mount 614 and fastened to the motor 605.

The motor mount 614 can be attached to the valve base 617. In FIG. 7A, the motor mount 614 can be attached to the valve base 617 with one or more base screws 651. The base screws 651 can be inserted through openings along the perimeter of the motor mount 614 and can be fastened into corresponding openings along the perimeter of the valve base 617. The valve base 617 can comprise a container with an inner cavity. Along its exterior, the valve base 617 can one multiple port openings.

The valve core 631 can be positioned within an inner cavity of the valve base 617. The valve core 631 can rotate within the cavity of the valve base 617 in order to align a fluid channel (FIG. 8) of the valve core 631 to one of the port connections 620. As the shaft 645 of the motor 605 turns, the valve core 631 is rotated. The valve core 631 also has a first groove 654a at one end and a second groove 654b (collectively "the grooves 654") at another end of the valve core 631. The core o-rings 625 are positioned within the grooves 654. The valve core 631 also includes peripheral openings 657 for inserting the magnets 633 within the valve core 631. The core o-rings 625 can create a fluid seal between the valve core 631 and the valve base 617.

The base o-ring 627 is positioned in a lower portion of the inner cavity of the valve base 617. The base o-ring 627 can create a fluid seal between the lower portion of the valve core 631 and the lower portion of the valve base 617.

The valve base 617 has port connections 620 around its peripheral. In the illustrated embodiment, the valve base 617 has three port connections 620 that are visible and one port connection 620 that is hidden from view. The number of port connections 620 can vary and the locations of the port connections 620 on the valve base 617 can vary. The port connections 620 can provide a fluid sealed connection to a tube 149, a water supply line 115, or other suitable tube connection. The port connection 620 can include a portion of the valve base 617, a gasket 636, a port 637, a port o-ring 639, and a fitting 642.

The port o-rings 639 can be positioned between the fitting 642 and the port 637. The gasket 636 can fit within a recessed area of the port 637. The port 637 can be welded to a perimeter of a port opening in the valve base 617. The valve base 617 can be attached to the mounting bracket 611 by one or more bracket fasteners 660. The position sensor 623 is attached to a sensor port 663 along the exterior of the valve base 617. The position sensor 623 can be coupled to the controller 118.

Moving on to FIGS. 7B through 7D, shown are different views of the adjustable valve assembly 602. Specifically, FIG. 7B illustrates a top-down view of the adjustable valve assembly 602. From the top-down view, a top portion of the motor 605, the motor mount 614 and the port connections 620 are viewable. Although four port connections 620 are shown, the number of connections can vary. For example, some embodiments can have three, five, six, seven, eight, nine, or more port connections 620. FIG. 7C illustrates a corresponding side view of the adjustable valve assembly 602 from FIG. 7B. FIG. 7D illustrates a corresponding bottom-up view of the adjustable valve assembly 602. From the bottom-up view in FIG. 7D, shown are aspects of the mounting bracket 611 and the tank port connection 622.

Figure 8:
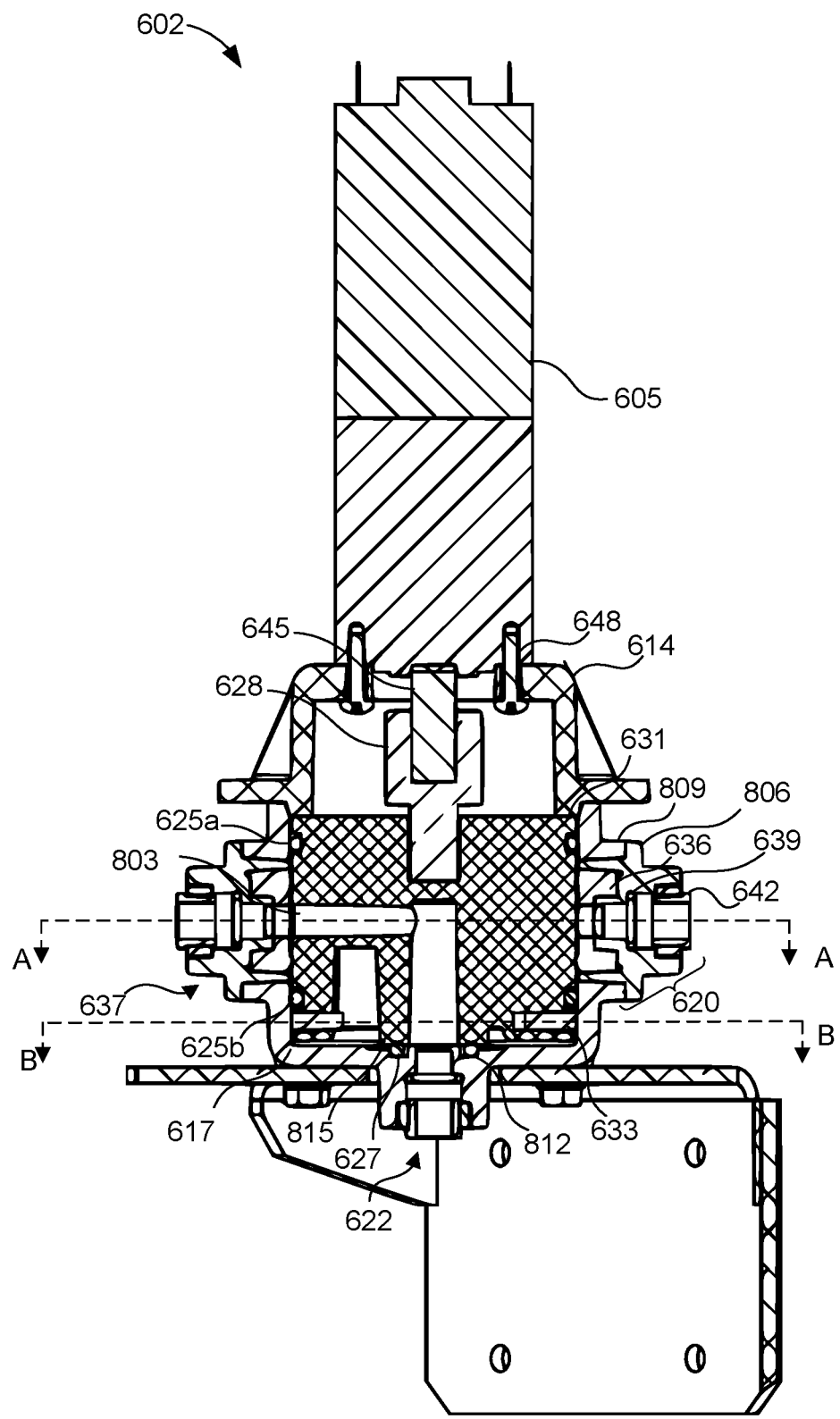
FIG. 8 illustrates a cross-sectional view of the adjustable valve assembly from FIG. 7A according to various embodiments of the present disclosure.

With reference to FIG. 8, shown is a cross-sectional view of the adjustable valve assembly 602 shown in FIGS. 6 and 7A-7D. FIG. 8 includes a first cross-sectional reference "AA" and a second cross sectional reference "BB" of the adjustable valve assembly 602. The first cross-sectional reference "AA" and the second cross-sectional reference "BB" are referenced in FIGS. 9A-9J. The first cross-sectional reference "AA" and the second cross-sectional reference "BB" refer to cross-sections at different heights of the adjustable valve assembly 602.

In the illustrated embodiment, the shaft 645 of the motor 605 is inserted through the motor mount 614 and attached to the motor coupler 628. Specifically, the motor coupler 628 is attached to the shaft 645 at a first end and the motor coupler 628 is attached to the valve core 631 at a second end. At the first end, the shaft 645 is inserted within a cavity of the motor coupler 628. At the second end, the motor coupler 628 has a lower portion with a reduced width, which is inserted into a cavity of the valve core 631.

FIG. 8 illustrates that the valve core 631 has a side opening and a bottom opening that are connected by a fluid channel 803. Although shown on the side, the side opening can be situated at other locations on the valve core 631. The side opening may also be referred to as a core port opening. The bottom opening of the fluid channel 803 can be connected to the tank port connection 622. The side opening of the fluid channel 803 can be aligned with any of the port connections 620 along the perimeter of the valve base 617. Once aligned, liquid or gas can flow in either direction. For example, liquid can flow from a port connection 620 through the fluid channel 803 and through the tank port connection 622, which in turn can travel to the tank 156. In another example, fluid can flow from the tank port connection 622 through the fluid channel 803 and through one of the port connections 620, which can lead to the water distribution system 127 as another non-limiting example.

Additionally, FIG. 8 illustrates the connections among the components of the port connections 620, which shown in an exploded view in FIG. 7A. The fitting 642 is attached to the port 637, in which the port o-ring 639 is positioned in between the components to provide a fluid seal. The fitting 642 can be a variety of fluid fittings, such as a John Guest fitting or other suitable fluid fittings. Next, the gasket 636 is positioned within a recessed portion of the port 637. The gasket 636 facilitates a fluid seal between the port connection 620 and the valve core 631. The gasket 636 can be comprised of rubber or other suitable materials.

As illustrated in FIG. 8, the port 637 comprises a flange 806, which can be attached to a rim 809 of the valve base 317. In some embodiments, these components can be attached using sonic welding techniques or other suitable techniques.

Further, FIG. 8 illustrates the interaction among the components with the core o-rings 625. The first core o-ring 625a is positioned in the first groove 654a (FIG. 7A) and the second core o-ring is positioned in the second groove 654b. The core o-rings 625 are positioned in between the valve core 631 and the interior surface of the valve base 617. Further, the base o-ring 627 is positioned in a recessed bottom portion 812 of the valve base 617. In this embodiment, the base o-ring 627 contacts an extended base 815 of the valve core 631. The extended base 815 is formed by an annular groove at the bottom of the valve core 631. The extended base 815 also has a greater height from the top of the valve core 631 than other portions of the bottom surface of the valve core 631.

Moving on to FIGS. 9A-9J, shown is an exemplary progression of the valve core 631 rotating within the valve base 617. FIGS. 9A, 9C, 9E, 9G, and 9I are in reference to the second cross-sectional reference "BB" shown in FIG. 8, particularly illustrating the rotation of the magnets 633 within the valve core 631 with the fluid channel 803 orientated at different positions. FIGS. 9B, 9D, 9F, 9H, and 9J are in reference to the first cross-sectional reference "AA" shown in FIG. 8, particularly illustrating the rotation of the fluid channel 803 within the valve core 631. FIGS. 9B, 9D, 9F, 9H, and 9J also illustrate that the fluid channel 803 can be oriented in an off state or in a state that allows fluid flow to one of the port connections 620.

With reference to FIGS. 9A and 9B, shown are views of the valve core 631 at different cross-sectional heights in a home or off state. As illustrated in FIG. 9A, the five magnets 633 are oriented along the perimeter of the valve core 631. The magnets 633 are positioned with a particular spacing arrangement for identifying the orientation of the valve core 631. The magnets 633 can be detected by the position sensor 623 when a magnet 633 is within a proximity to the position sensor 623. In the illustrated example of FIGS. 9A and 9B, the positioning of magnet 633b shown in FIG. 9A corresponds to the location of the side opening for the fluid channel 803 shown in FIG. 9B. In some embodiments, a controller 118 can identify the position of the fluid channel 803 by rotating the valve core 631 at a constant rate and timing the detection of the magnets 633. For instance, it shall be assumed that the valve core 631 is rotating in a clockwise direction. The first distance between magnet 633c and magnet 633d is less than a second distance between magnet 633d and magnet 633e. With a shorter distance, the period of time to detect magnet 633c after magnet 633d is less than the period of time between other magnets 633, such as between magnet 633d and magnet 633e. After identifying a shorter detection period, the controller 118 can determine that the next detected magnet 633b corresponds to the location of the side opening for the fluid channel 803. It should be noted that the positioning of the magnets 633 can vary and the position detection scheme for the valve core 631 can vary as well.

With reference to FIGS. 9A-9J, the adjustable valve assembly 602 can be configured in different combinations of tubes attached to the port connections 620 and the tank port connection 622. For example, referring to FIG. 9B, a first configuration can involve attaching port connection 620a to a water outlet line 115a, attaching port connection 620b to the spores container 106 via the second tube 149b, attaching port connection 620c to the nutrient container 103 via the first tube 149a, and attaching port connection 620d to a water outlet line 115b.

In this first configuration, the port connection 620d operates as a dedicated water inlet line 115a that provides water from the water supply 131 to the adjustable valve 608, which can then be provided to the tank 156. Port connection 620a operates as a dedicated water outlet line 115b that provides a dosage mixture or water from the adjustable valve 608 to the water distribution system 127.

As another example, a second configuration can include using port connection 620a as a vent, attaching port connection 620b to the spores container 106 via the second tube 149b, attaching port connection 620c to the nutrient container 103 via the first tube 149a, and attaching port connection 620d to the water supply line 115 that serves to as a water inlet line and a water outlet line.

In this second configuration, the port connection 620a can serve as a vent to depressurize the adjustable valve 608 prior to initiating a dosage cycle, in between steps in a dosage cycle, or after the completion of the dosage cycle. Accordingly, the port connection 620d can operate as a water inlet port and a water outlet port as described in other embodiments in the present disclosure.

As shown, FIGS. 9A and 9B represent an off or home state as one exemplary configuration. In the home state, the side opening of the fluid channel 803 is oriented to face the inner surface of the valve base 617. Accordingly, the fluid channel 803 is not aligned with any of the port connections 620.

Figure 9E:
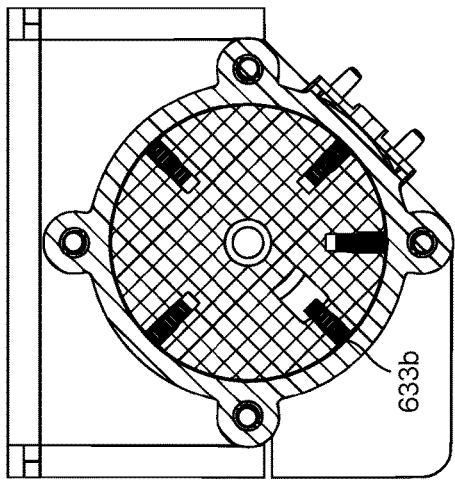
Figure 9F:
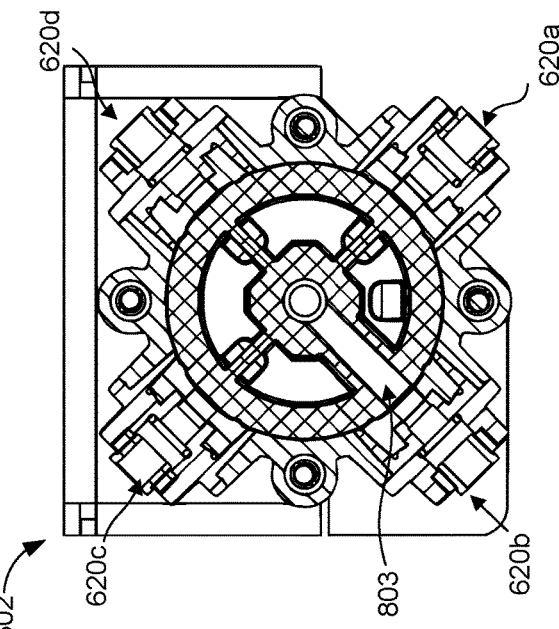
Figure 9C:
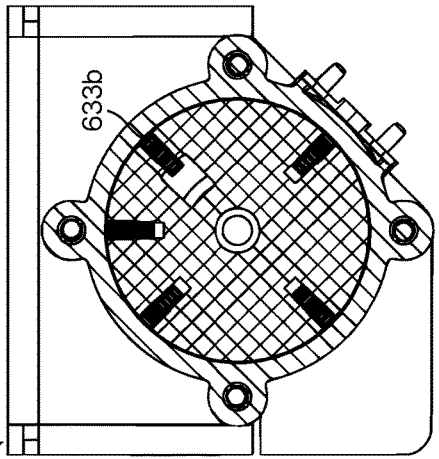
Figure 9D:
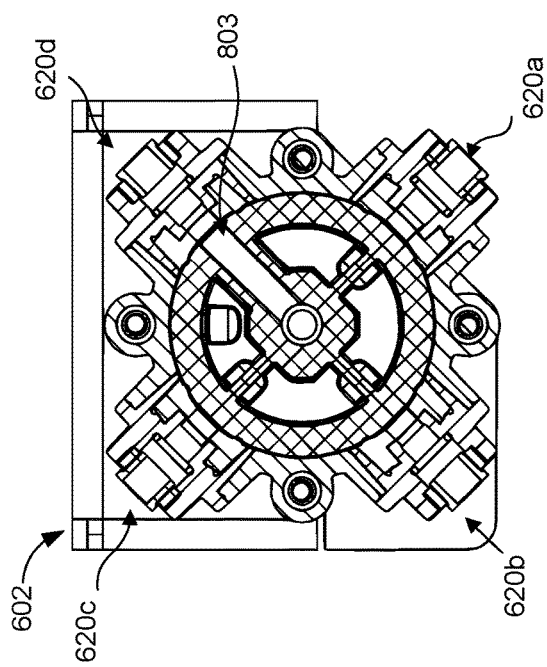

In FIGS. 9C and 9D, the fluid channel 803 has been moved to a different location, in which the valve core 631 has been rotated within the valve base 617. In FIG. 9C, the magnets 333 have also rotated to reflect the different orientation of the valve core 631. Thus, magnet 333b has been rotated to a new location. Continuing with the previous discussion of the first configuration, the fluid channel 803 can be in a water inlet state. Thus, the fluid channel 803 is aligned with the port connection 620d. In this state, the fluid channel 803 is enable to receive water from the water supply 131 and the fluid channel 803 can provide the water to the tank 156 through the tank port connection 622.

In FIGS. 9E and 9F, the fluid channel 803 has been moved to a different location, in which the valve core 631 has been rotated within the valve base 617. In FIG. 9E, the magnets 333 have also rotated to reflect the different orientation of the valve core 631. Thus, magnet 333b has been rotated to a new location. Continuing with the previous discussion of the first configuration, the fluid channel 803 can be in a spores state. Thus, the fluid channel 803 is aligned with the port connection 620b. In this state, the fluid channel 803 is enable to receive spores from the spores container 106 and the fluid channel 803 can provide the spores to the tank 156 through the tank port connection 622.

Figure 9I:
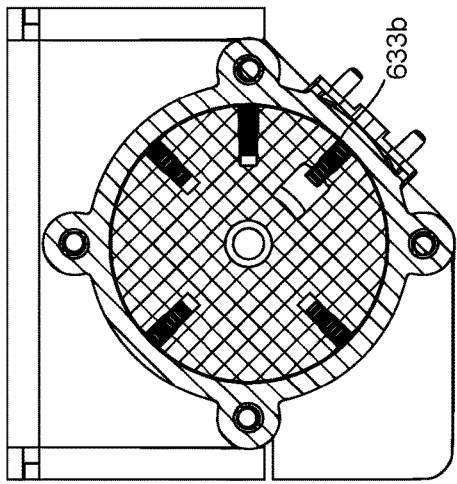
Figure 9J:
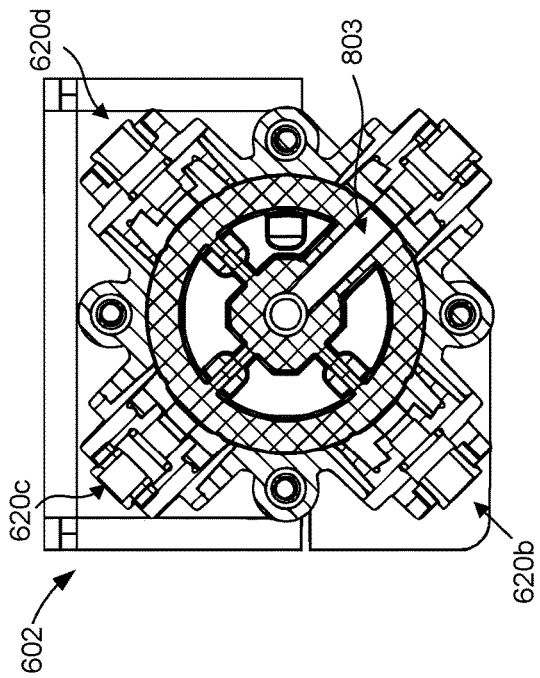
Figure 9G:
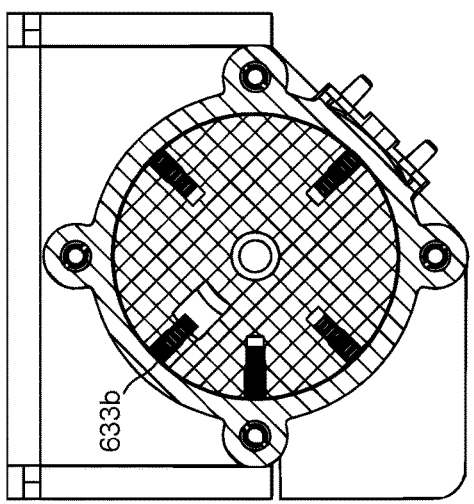
Figure 9H:
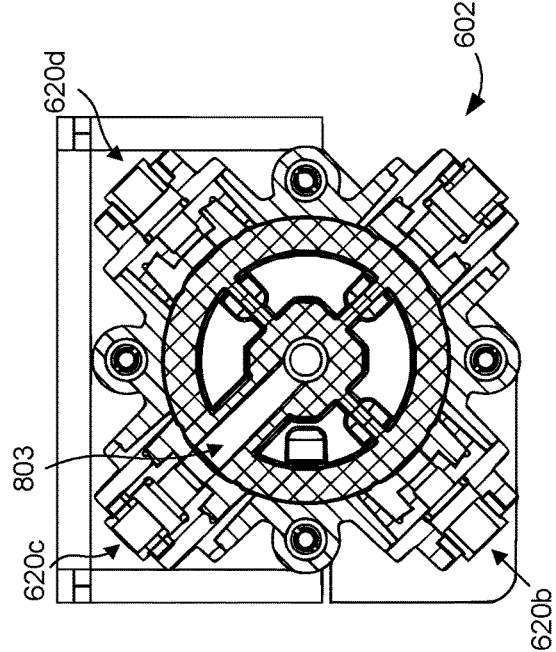

In FIGS. 9G and 9H, the fluid channel 803 has been moved to a different location, in which the valve core 631 has been rotated within the valve base 617. In FIG. 9G, the magnets 333 have also rotated to reflect the different orientation of the valve core 631. Thus, magnet 333*b* has been rotated to a new location. Continuing with the previous discussion of the first configuration, the fluid channel 803 can be in a nutrient state. Thus, the fluid channel 803 is aligned with the port connection 620*c*. In this state, the fluid channel 803 is enable to receive nutrients from the nutrients container 103 and the fluid channel 803 can provide the nutrients to the tank 156 through the tank port connection 622.

In FIGS. 9I and 9J, the fluid channel 803 has been moved to a different location, in which the valve core 631 has been rotated within the valve base 617. In FIG. 9I, the magnets 333 have also rotated to reflect the different orientation of the valve core 631. Thus, magnet 333*b* has been rotated to a new location. Continuing with the previous discussion of the first configuration, the fluid channel 803 can be in a water outlet state. Thus, the fluid channel 803 is aligned with the port connection 620*a*. In this state, the fluid channel 803 is enable to receive a dosage mixture or water from the tank 156 and the fluid channel 803 can provide the dosage mixture or water to the water distribution system 127 through the port connection 620*a*.

Moving on to FIGS. 10A through 10F, shown are various views of the valve base 617 from FIGS. 6, 7A, 7B, 8, and FIGS. 9A through 9J. FIG. 10A illustrates a top view of the valve base 617. Further, FIG. 10B illustrates a perspective view of the valve base 617, and FIG. 10C a side view of the valve base 617. FIG. 10D illustrates a cross-sectional view of the valve base 617. FIG. 10E a bottom-up view of the valve base 617. FIG. 10F illustrates a side view of the valve base 617, which is oriented upside down from FIG. 10D.

In FIGS. 10A, 10D, 10E, and 10F, the sensor port 663 is indicated as an orientation reference. FIG. 10A illustrates the interior cavity of the valve base 617 from a top-down view and FIG. 10B illustrates the interior cavity of the valve base 617 from a perspective view. FIGS. 10A through 10F provide different views of the rims 809 that surrounds port openings in the valve base 617. In some embodiments, the rim 809 is welded to the flange 806 of a port 637. Further, in FIG. 10D, the recessed bottom portion 812 is visible, in which the base o-ring 627 is omitted. The recessed bottom portion 812 surrounds the bottom port opening for the valve base 617.

Turning to FIGS. 11A through 11F, shown are various views of the motor mount 614. FIG. 11A illustrates a top view of the motor mount 614. Further, FIG. 11B illustrates a perspective view of the motor mount 614. FIG. 11C illustrates a first side view of the motor mount 614, and FIG. 11D illustrates a second side view of the motor mount 614. FIG. 11E illustrates a bottom-up view of the motor mount 614. FIG. 11F illustrates a cross-sectional view of the motor mount 614, which is oriented upside-down with respect to FIG. 11C.

Figure 6:
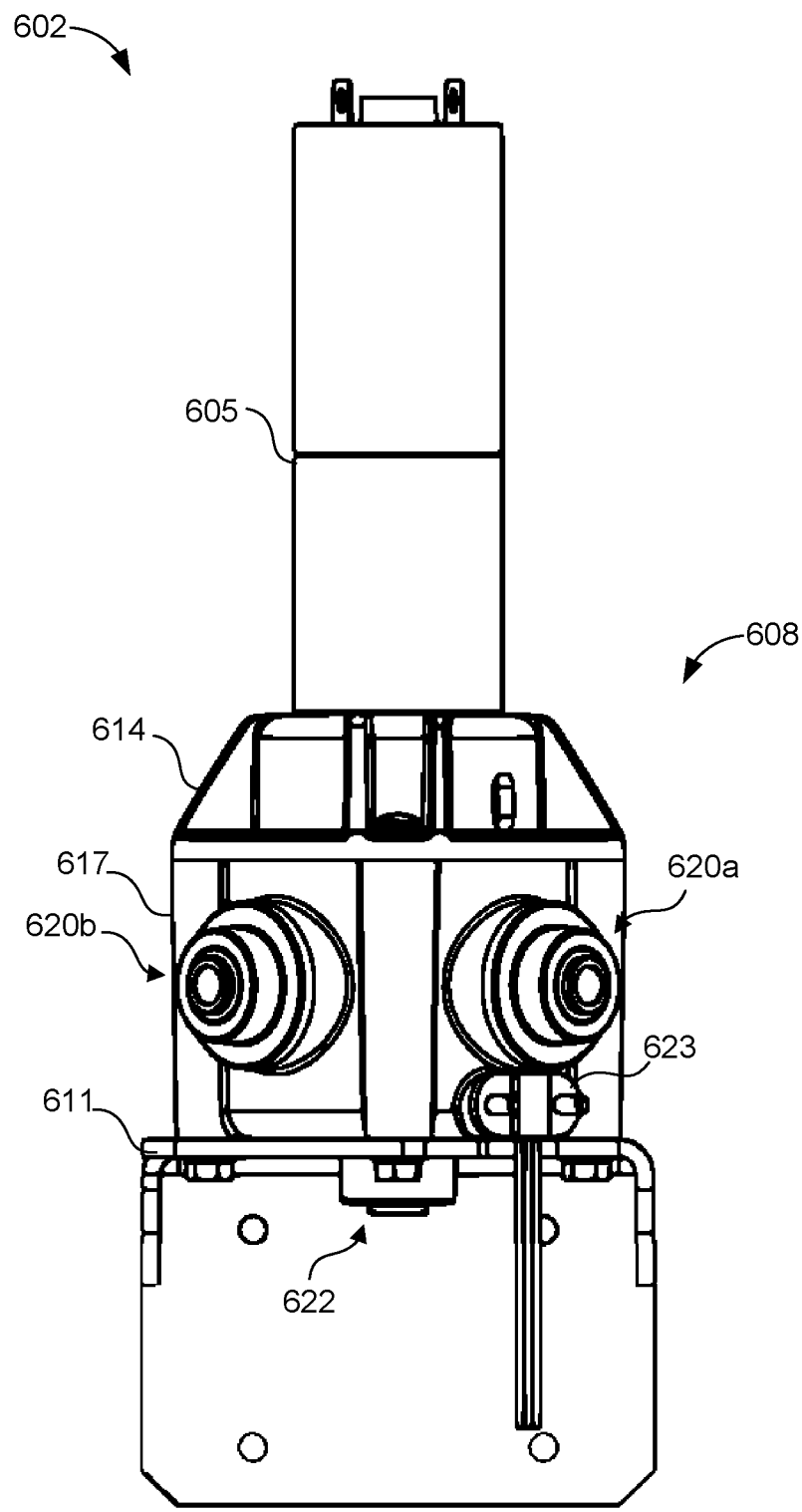
FIG. 6 illustrates a front view of an adjustable valve assembly according to various embodiments of the present disclosure.

With respect to FIGS. 11A through 11F, the motor mount 614 is shown to have a top platform and a bottom platform. The top platform has opening that are used for attaching the motor 605 via the motor mount screws 648 (FIGS. 6 and 7A). The bottom platform has openings that are used for attaching the motor mount 614 to the valve base 617 (FIGS. 6 and 7A) via the base screws 651.

Moving on to FIGS. 12A through 12F, shown are various views of the valve core 631. FIG. 12A illustrates a perspective view of the valve core 631, and FIG. 12B illustrates a top-down view of the valve core 631 from FIG. 12A. FIG. 12C illustrates a first cross-sectional view of the valve core 631, in which the valve core 631 from FIG. 12A is oriented upside-down. FIG. 12D illustrates a side view of the valve core 631, and FIG. 12E illustrates a second cross-sectional view of the valve core from FIG. 12D. FIG. 12F illustrates a bottom-up view of the valve core 631.

Referring to FIGS. 12A through 12F, shown is a coupler opening 1203 for receiving a portion of the motor coupler 628 (FIG. 7A). The valve core 631 also comprises a side or core opening 1206 for the fluid channel 803 (FIG. 8). The fluid channel 803 connects the side opening 1206 to the bottom opening 1212. The side opening 1206 can be aligned to one of the port connections 620 or oriented in an off state, in which the side opening 1206 is facing the interior wall of the valve base 617. The valve core 631 has also multiple peripheral opening 657 for inserting magnets 633.

Further, the valve core 631 can also have an extended base 815. The extended base 815 extends past the bottom surface of the valve core 631. The extended base 815 can be positioned on the base o-ring 627 in order to create a water seal around the bottom opening 1212 of the fluid channel 803.

Figure 13A:
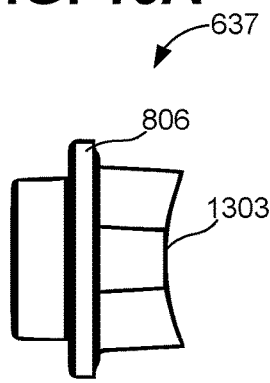
Figure 13B:
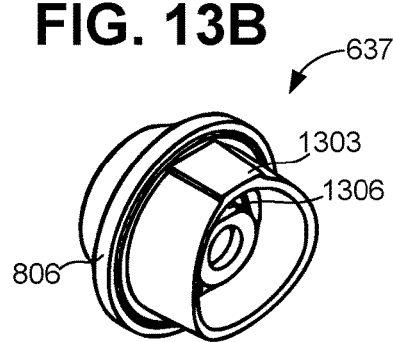
Figure 13C:
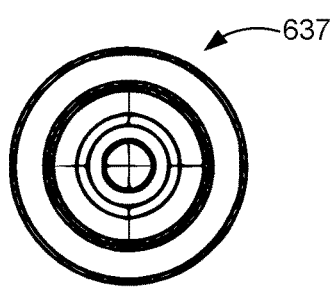
Figure 13D:
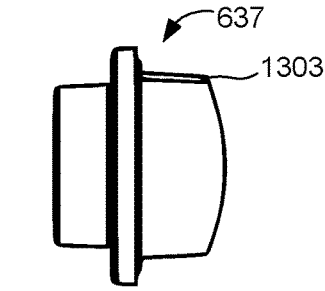
Figure 13E:
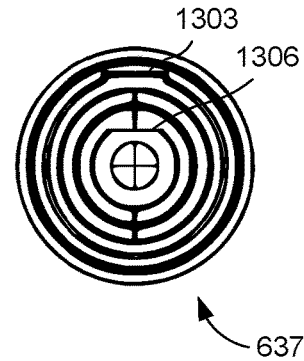
Figure 13F:
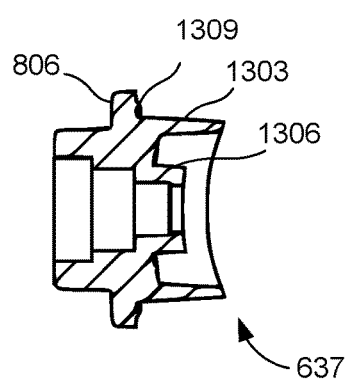

Moving on to FIGS. 13A through 13F, shown are various views of the port 637. FIG. 13A illustrates a top-down view of the port 637, and FIG. 13B illustrates a perspective view of the port 637. FIG. 13C illustrates a front view of the port 637, and FIG. 13D illustrates a side view of the port 637 in shown in FIG. 13C. FIG. 13E illustrates a rear view of the port 637, and FIG. 13F display a cross-sectional view of the port 637.

FIG. 13A displays that the port 637 has an upper platform 1303 and a lower platform 1306. The upper platform 1303 and the lower platform 1306 are used to ensure that the gasket 636 is inserted in the correct orientation into the port 637. The upper platform 1303 is connected to an outer circular rim. The lower platform 1306 is connected to an inner circular rim, which is recessed within port 637 with respect to the outer circular rim. Thus, the inner circular rim has a smaller diameter than the outer circular rim. Additionally, from the rear side, the port 637 has an annular protrusion 1309 that can be used to mate with the gasket 636.

Figure 14B:
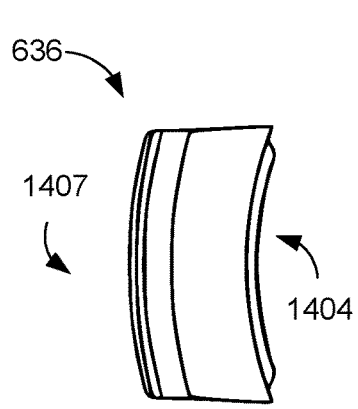
Figure 14A:
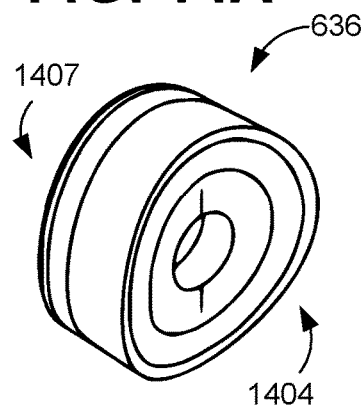
Figure 14D:
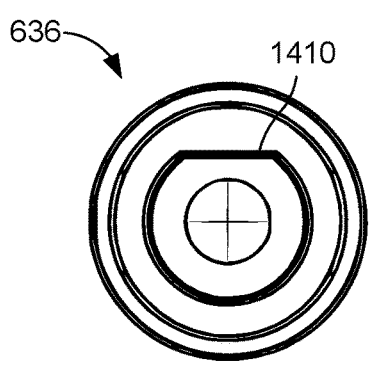
Figure 14C:
Figure 14E:
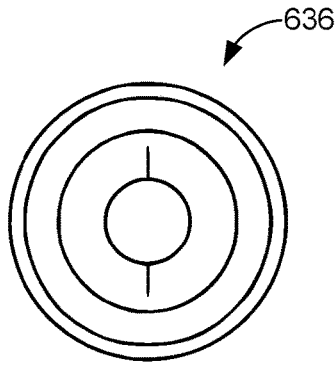
Figure 14F:
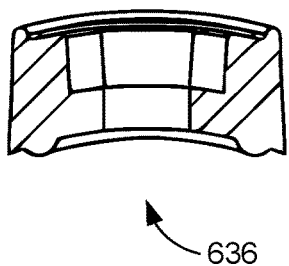

Turning to FIGS. 14A through 14F, shown are various views of the gasket 636. FIG. 14A illustrates a perspective view of the gasket 636. FIG. 14B illustrates a first side view and FIG. 14C illustrates a second side view of the gasket 636. FIG. 14D illustrates a rear view of the gasket 636, and FIG. 14E illustrates a front view of the gasket 636. FIG. 14F illustrates a cross-sectional view of the gasket 636.

The gasket 636 has a port side 1404 and a valve side 1407. The port side 1404 connects with the port 637, particularly being inserted within a recessed area of the port 637. The valve side 1407 contacts the valve core 631 that is within the valve base 617. The valve side 1407 of the gasket 636 has a concave shape to conform to the curvature of the valve core 631. Thus, the valve side 1407 of the gasket 636 can make contact with the entire perimeter of the side opening of the valve core 631. The gasket 636 helps maintain a fluid seal for the port connection 620. The gasket 636 can be comprised of rubber, plastic, and other suitable materials.

FIG. 14D illustrates a front view of the port side 1404. As shown, the port side 1404 of the gasket 636 has an intermediate platform 1410. The intermediate platform 1410 is connected to an annular rim. The intermediate platform 1410 can be positioned below the upper platform 1303 and above the lower platform 1306 (FIG. 13F) of the port 637. When the gasket 636 is inserted within the port 637, the upper platform 1303, the intermediate platform 1410, and the lower platform 1306 can be parallel to each other.

Moving to FIGS. 15A through 15D, shown are various views of the mounting bracket 611. FIG. 15A illustrates a perspective view of the mounting bracket 611. FIG. 15B illustrates a top-down view and FIG. 15C illustrates a side view of the mounting bracket 611 FIG. 15D illustrates a front view of the mounting bracket 611.

Turning to FIG. 16A through 16E, shown are various views of the motor coupler 628. FIG. 16A illustrates a perspective view and FIG. 16B illustrates a top down view of the motor coupler 628. FIG. 16C illustrates a cross-sectional view and FIG. 16D illustrates a side view of the motor coupler 628. FIG. 16E illustrates a bottom-up view of the motor coupler 628.

As illustrated, the motor coupler 628 comprises a cylinder 1605 attached to a coupler shaft 1608, in which the coupler shaft 1608 has a width less than the diameter of the cylinder 1605. The cylinder 1605 has a cavity 1611 for receiving the shaft 645 of the motor 605. The cylinder 1605 also has threaded openings 1614 for inserting fasteners in order to secure the shaft 645 to the motor coupler 628. As illustrated, the coupler shaft 1608 has a rectangular shape. It should be noted that the shape of the motor coupler 628 can vary. The motor coupler 628 can be comprised of metal, plastic, a combination of materials, or other suitable materials.

Referring next to FIG. 17, shown is a flowchart that provides one example of the operation of the controller 118 according to various embodiments. The controller 118 can control a system 100 that includes, among other components, at least one of the adjustable valve 112, the alternative adjustable valve 430, or the adjustable valve assembly 602. It is understood that the flowchart of FIG. 17 provides merely an example of the many different types of functional arrangements that may be employed to implement the operation of a portion of the controller 118 as described herein. As an alternative, the flowchart of FIG. 17 can be viewed as depicting an example of elements of a method implemented in the controller 118 (FIG. 1A) according to one or more embodiments.

Beginning with box 1703, the controller 118 can detect a triggering condition to execute the system 100, which includes the adjustable valve assembly as one non-limiting example. Some non-limiting examples of triggering conditions may include a timer configured to initiate a dosage cycle on a periodic interval, on a schedule, animal activity, human activity, plant activity, water flow, an estimated drinking start time, an estimated peak drinking time, a drinking time based on a sunrise time, or on some other suitable basis. Additionally, the embodiments described herein can also be used for water treatment, drain treatment, and dispensing biologicals or chemicals. In another example, the system 100 can initiate a dosage cycle according to water consumption profile for a location, a type of animal, or other suitable water conditions. For this discussion, it is assumed that the adjustable valve assembly 602 is presently in a home (off) state and the syringe pump 109 is fully down. It is also assumed that the port configurations 620 are arranged according to the first configuration as discussed with respect to FIGS. 9A and 9B, in which the port connection 620d is connected to a water inlet line 115a (FIG. 1A) and port connection 620a is connected to a water outlet line 115b (FIG. 1A).

In box 1706, the controller can detect that the adjustable valve 608 (FIG. 6) is at a home (off) state. The home state can also indicate that the plunger 309 is adjacent to the base 312 (FIG. 3A).

In box 1709, the controller 118 can move the adjustable valve 608 to the water inlet port connection 620d and draw a volume of water into the tank 156 from the water supply line 115a. In some embodiments, the syringe pump 109 can draw in about 16 ml for a dosage.

In box 1712, the controller 118 can move the adjustable valve 608 to the spores port connection 620b and draw a volume of spores into the tank 156 from the spores container 106. In some embodiments, the syringe pump 109 can draw in about 20 ml.

In box 1715, the controller 118 can move the adjustable valve 608 to the nutrient port connection 620c and draw a volume of nutrients into the tank 156 from the nutrient container 103. In some embodiments, the syringe pump 109 can draw in about 5 ml.

In box 1718, the controller 118 can move the adjustable valve 608 to the water inlet port connection 620d and draw a volume of water into the tank 156. In some embodiments, the syringe pump 109 can draw in about 30 ml.

In box 1721, the controller 118 can move the adjustable valve 608 to the water outlet port connection 620a and agitate the mixture in the tank 156. In some examples, the syringe pump 109 is moved up and down in short movements to mix the different elements in the tank 156. The syringe pump 109 can travel about 0.1 inches in either direction as an example. In some embodiments, at this stage, the solution in the tank 156 does not get expelled into the water distribution system 127 at this stage.

In box 1724, the controller 118 can heat the mixture to a predefined temperature using the heater 141. In some embodiments, the heater 141 maintains the predefined temperature for a period of time in order to active the spores. For example, after the heater 141 is turned on, the controller 118 can receive measurement from the thermocouple 151. The controller 118 can heat the tank 156 until the solution reaches 36 degrees Celsius, as a non-limiting example. After reaching the desired temperature, the heater 141 is turned off.

In box 1727, the controller 118 can move the adjustable valve 608 to the water inlet port connection 620d and draw a volume of water into the tank 156. The water is drawn in to lower the temperature of the mixture.

In box 1730, the controller 118 can move the adjustable valve 608 to the water outlet port connection 620a and expel the mixture from the tank 156 to the water distribution system 127. The mixture can be expelled at different rates depending on the application.

In box 1733, the controller 118 can move the adjustable valve 608 to the water inlet port connection 620d and draw a volume of water into the tank 156. At this stage, the controller 118 can draw in water in order to rinse the tank 156. In box 1736, the controller 118 can move the adjustable valve 608 to the water outlet port connection 620a and expel the mixture from the tank 156 in order to expel the water used for rinsing the tank 156. In some examples, steps 1733 and 1730 may be repeated multiple times. For example, mixtures that are made for a particular type of animal may require 10 rinse and purge cycles. After the rinse and purge cycle has been completed, the controller 118 can move the adjustable valve 608 to the home (off) state. The controller 118 can go into an idle state to wait for the next trigger condition. Then, the proceeds to the end.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims. In addition, all optional and preferred features and modifications of the described embodiments and dependent claims are usable in all aspects of the disclosure taught herein. Furthermore, the individual features of the dependent claims, as well as all optional and preferred features and modifications of the described embodiments are combinable and interchangeable with one another.

Therefore, the following is claimed:

1. A system, comprising:
   a spores container to store a solution of spores;
   a nutrient container to store a solution of nutrients;
   a water source;
   a syringe pump comprising a tank, the tank being configured to receive a volume of the solution of spores, a volume of the solution of nutrients, and a volume of water;
   a heater to heat a mixture of the solution of spores, the volume of the solution of nutrients, and the volume of water in the tank;
   an adjustable valve configured to controllably open and close a first channel from the tank to the spores container, a second channel from the tank to the nutrient container, and a third channel from the tank to the water source; and a controller configured to control a sequence of operations among the adjustable valve and the syringe pump to form and activate a dosage of the mixture, the syringe pump being configured to draw the volume of the solution of spores, the volume of the solution of nutrients, and the volume of water from the adjustable valve and into the tank, the syringe pump being configured to expel the mixture from the tank to the adjustable valve, the controller being configured to determine a set temperature for the heater based at least in part on reaching a desired temperature for the mixture in the tank within a particular period of time.

2. The system of claim 1, wherein the adjustable valve comprises a position sensor to detect that the adjustable valve is situated in at least one of a neutral state, in a first position that opens the first channel from the tank to the spores container, in a second position that opens the second channel from the tank to the nutrient container, or in a third position that opens the third channel from the tank to the water source.

3. The system of claim 1, wherein the adjustable valve comprises a rotary valve.

4. The system of claim 1, wherein the adjustable valve comprises a linear piston.

5. The system of claim 1, further comprising:

a flow meter configured to provide a measurement of water consumption in a water distribution system, and wherein the controller is further configured to at least:

receive the measurement of water consumption from the flow meter; and initiate a respective dosage of the mixture based at least in part on the measurement of water consumption, wherein the respective dosage of the mixture is provided to the water distribution system.

6. The system of claim 1, wherein the syringe pump comprises a plunger and a proximity sensor to detect a position of the plunger in the tank.

7. The system of claim 1, wherein the controller is further configured to determine the set temperature for the heater based at least in part on at least one of a water supply temperature of a water supply line, a water temperature of the water source, or an outdoor temperature.

8. The system of claim 1, wherein the controller is configured to at least initiate a respective dosage of the mixture through a water supply line to a water distribution system based at least in part on a profile of water consumption for at least one animal.

9. The system of claim 1, wherein the controller is configured to at least initiate a respective dosage of the mixture to a water distribution system based at least in part on a profile of water consumption for at least one plant, wherein the respective dosage of the mixture is pushed through a check value and into the water distribution system.

10. The system of claim 1, wherein the controller is configured to at least initiate a respective dosage of the mixture into a water distribution system based at least in part on a profile of water consumption for at least one human.

11. The system of claim 1, wherein the sequence of operations for forming and activating the dosage of the mixture is initiated based at least in part on at least in one of a motion sensor, a sound sensor, a light sensor, and a timer.

12. The system of claim 1, wherein the adjustable valve comprises a first port that connects to the water source for incoming water and the adjustable valve comprises a second port that connects to a water outlet line for supplying outgoing water to a water distribution system for at least one animal.

13. The system of claim 1, wherein, in a dosage state, the controller is configured to determine the sequence of operations for drawing the volume of the solution of spores, the volume of the solution of nutrients, and the volume of water into the tank based at least in part on a profile for an animal.

14. The system of claim 1, wherein, in a dosage state, the controller is configured to determine the sequence of operations for drawing the volume of the solution of spores, the volume of the solution of nutrients, and the volume of water into the tank based at least in part on a profile for plant consumption.

15. The system of claim 1, wherein, in a dosage state, the controller is configured to determine the sequence of operations for drawing the volume of the solution of spores, the volume of the solution of nutrients, and the volume of water into the tank based at least in part on a profile of human consumption.

16. The system of claim 1, wherein the syringe pump comprises a threaded shaft with a plunger at one end, the threaded shaft being in a threaded engagement with a pump motor.

17. The system of claim 1, wherein, in an activation state, the mixture is heated at an elevated temperature for a predefined period of time.

18. The system of claim 17, wherein, in a cooling mixture state, the controller is configured to at least:
   cause the adjustable valve to open the third channel from the tank to the water source; and
   cause the syringe pump to draw an amount of water in the tank.

19. The system of claim 18, wherein, in a dispensing state, the controller is configured to cause the syringe pump to expel the mixture from the tank through the adjustable valve and to the water source.

20. A system, comprising:
   a first container to store a first solution;
   a second container to store a second solution;
   a water source;
   a syringe pump comprising a tank, the tank being configured to receive a volume of the first solution, a volume of the second solution, and a volume of water;
   a heater;
   an adjustable valve configured to controllably open and close a first channel, a second channel, and a third channel to form a mixture of the volume of the first solution, the volume of the second solution, and the volume of water in the tank; and
   a controller configured to control a sequence of operations among the adjustable valve and the syringe pump to form and activate a dosage of the mixture, the syringe pump being configured to draw the volume of the first solution, the volume of the second solution, and the volume of water from the adjustable valve and into the tank, the syringe pump being configured to expel the mixture from the tank to the adjustable valve, the controller being configured to determine a set temperature for the heater based at least in part on at least one of a water supply temperature of a water supply line, a water temperature of the water source, or an outdoor temperature.

\* \* \* \* \*